(12) United States Patent  
Bartra Sanmarti et al.

(10) Patent No.: US 9,035,070 B2  
(45) Date of Patent: May 19, 2015

(54) PROCESS FOR THE PREPARATION OF 1-ARYL-PYRAZOL-3-ONE INTERMEDIATES USEFUL IN THE SYNTHESIS OF SIGMA RECEPTORS INHIBITORS

(75) Inventors: Martí Bartra Sanmarti, Barcelona (ES); Ramon Berenguer Maimo, Barcelona (ES); Jorge Medrano Ruperez, Barcelona (ES); Jorge Garcia Gomez, Barcelona (ES); Javier Ariza Piquer, Barcelona (ES)

(73) Assignee: ESTEVE QUÍMICA, S.A., Barcelona (ES)

( * ) Notice: Subject to any disclaimer, the term of this patent is extended or adjusted under 35 U.S.C. 154(b) by 55 days.

(21) Appl. No.: 13/704,148

(22) PCT Filed: Jul. 28, 2011

(86) PCT No.: PCT/EP2011/063020  
§ 371 (c)(1),  
(2), (4) Date: Mar. 4, 2013

(87) PCT Pub. No.: WO2012/013755  
PCT Pub. Date: Feb. 2, 2012

(65) Prior Publication Data  
US 2013/0184472 A1    Jul. 18, 2013

(30) Foreign Application Priority Data  
Jul. 30, 2010   (EP) .................................. 10382211

(51) Int. Cl.  
*C07D 231/20* (2006.01)  
*C07D 207/36* (2006.01)  
*C07D 317/30* (2006.01)

(52) U.S. Cl.  
CPC ............ *C07D 207/36* (2013.01); *C07D 231/20* (2013.01); *C07D 317/30* (2013.01)

(58) Field of Classification Search  
None  
See application file for complete search history.

(56) References Cited

FOREIGN PATENT DOCUMENTS

| DE | 4445930 | 6/1996 |
|---|---|---|
| GB | 1151095 | 7/1966 |
| WO | WO 2006/021462 A1 | 3/2006 |
| WO | WO2007098953 | 9/2007 |
| WO | WO2009130314 | 10/2009 |

OTHER PUBLICATIONS

Udeta, T et al., "Synthesis of Pyrazolone Derivatives, LKII. Synthesis and Analgesic Activity of 2-Methyl-1-phenyl-6,7-dihydro-1H,5H-pyrazolo[5,1-b][1,3] oxazin-8-ium Bromide", Journal of the Pharmaceutical Society of Japan 1982, vol. 102 (8), pp. 743-747.  
Mahindra, T. Makhija et al., De novo design and synthesis of HIV-1 integrase inhibitors, Bioorganic & Medicinal Chemistry, Pergamon, GB, vol. 12, Jan. 1, 2004, pp. 2317-2333.

*Primary Examiner* — Kamal Saeed  
(74) *Attorney, Agent, or Firm* — Timothy H. Van Dyke; Beusse, Wolter, Sanks & Maire, P.A.

(57) ABSTRACT

The invention relates to a process for preparing 1-aryl-pyrazol-3-one intermediates, tautomers, and salts thereof, to novel intermediates, and to the use of the intermediates in the preparation of sigma receptor inhibitors.

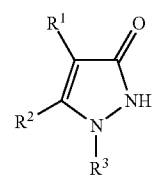

(VII)

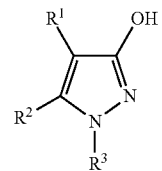

(VIIa)

15 Claims, No Drawings

PROCESS FOR THE PREPARATION OF 1-ARYL-PYRAZOL-3-ONE INTERMEDIATES USEFUL IN THE SYNTHESIS OF SIGMA RECEPTORS INHIBITORS

CROSS-REFERENCE TO RELATED APPLICATIONS

This application is a national stage entry of PCT/EP2011/063020 filed Jul. 28, 2011, and is related to European Patent application No. 10382211.0 filed Jul. 30, 2010, to which priority is claimed under 35 USC 119.

FIELD OF THE INVENTION

The invention relates to a process for preparing 1-aryl-pyrazol-3-one intermediates, tautomers, and salts thereof, to novel intermediates, and to the use of the intermediates in the preparation of sigma receptor inhibitors.

BACKGROUND OF THE INVENTION

Psychiatric and neurologic disorders are among the most severe and chronic diseases and conditions. These disorders are also extremely difficult to treat effectively because of the multiplicity of the symptoms and etiologies.

Amongst the therapeutic arsenal to combat these psychiatric and neurologic disorders, sigma receptors inhibitors have been found useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews,* 1990, 42, 355).

WO2006021462 and WO2007098953 describe pyrazole-containing compounds having pharmacological activity towards the sigma receptor, being particularly useful in the therapy of pain, in particular neuropathic pain or allodynia. These compounds have the following chemical structure:

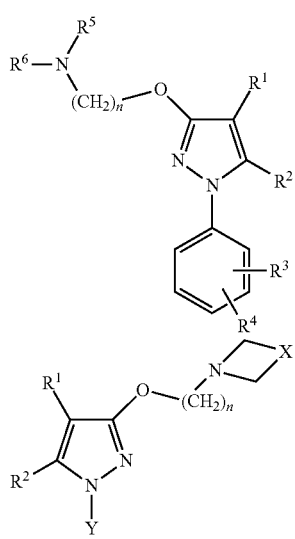

These compounds may be prepared according to the route schemes disclosed in WO2006021462 and WO2007098953. Of particular interest are the intermediates represented by the formula (II) in said patent applications (further referred as final intermediates):

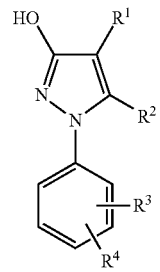

wherein $R^3$ and $R^4$ are independently halogen or $C_{1-6}$alkoxy, or together with the phenyl to which they are attached to, they form an optionally substituted naphthyl ring.

According to the routes presented in the mentioned patent applications, these intermediates can be prepared by reacting an acetohydrazide derivative with an ethyl acetoacetate; by reacting an hydrazine derivative with an ethyl butynoate; or by the method provided by F. Effenberger and W. Hartmann, *Chem. Ber.,* 102(10), 3260-3267, 1969, where an ethoxyacrylic acid hydrazide is reacted with concentrated mineral acid.

When considering different routes for the preparation of the 1-aryl-pyrazol-3-one intermediates referred above, one approach is to directly react an arylhydrazine with a ketoacetate. However, this shortcut presents the drawback that being the distal nitrogen of hydrazine the most reactive atom, it will preferably react with the ketone carbonyl of ketoacetate—more electrophilic—rather than with the ester carbonyl of the same reagent, as it would be desired. The non-desired reaction results in an enamine that after cyclization yields the non-desired isomer of 1-aryl-pyrazol-3-one intermediates, i.e. 1-aryl-pyrazol-5-one (depicted below). This reaction was reproduced by the inventors and it is also described in *Bioor. and Med. Chem.* 2004, 2317.

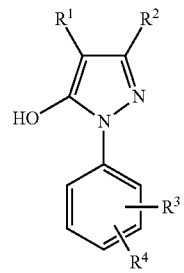

As such, because of this undesired reaction, the solution proposed by WO2006021462 and WO2007098953, protects the arylhydrazine by converting it into an acetohydrazide, thereby forcing a reaction between the proximal nitrogen atom of the hydrazide—now more reactive—with the ketone carbonyl of ethyl acetoacetate. An enamine is formed, which is submitted to energetic acidic conditions in order to be cyclised and thereby results into the 1-aryl-pyrazol-3-one intermediate. Such energetic conditions generate a significant amount of by-products that consequently diminish the reaction yield.

WO2009130314 (Laboratorios del Dr. Esteve) relates to a process for preparing naphthalen-2-yl-pyrazol-3-one intermediates, tautomers, and salts thereof, to novel intermediates, and to the use of the intermediates in the preparation of sigma receptor inhibitors. This alternative route comprises in particular submitting 2-methyl-2-(naphthalen-2-yldiazenyl)furan-3(2H)-ones to acidic conditions.

Ueda et al. (Synthesis of pyrazolone derivatives. XLII. Synthesis and analgesic activity of 2-methyl-1-phenyl-6,7-dihydro-1H,5H-pyrazolo[5,1-b][1,3]oxazin-8-ium bromide. Yakugaku Zasshi (1982), 102(8), 743-7) proposes in Chart I of page 744 and in the last two paragraphs on page 745, the reaction of an ethyl 2-(2-methyl-1,3-dioxolan-2-yl)acetate with phenylhydrazine in the presence of sodium methoxide as a base and benzene as a solvent, thereby obtaining 2-(2-methyl-1,3-dioxolan-2-yl)-N'-phenylacetohydrazide, which is further cyclised after treatment with hydrochloric acid 10% and heating on a water bath at 90° C., to obtain 3-hydroxy-5-methyl-1-phenylpyrazole. However, this method presents the disadvantage that both sodium methoxide and benzene are unsuitable for industrial upscaling, in particular, sodium methoxide is a dangerous and highly toxic reagent and benzene is carcinogenic and therefore unsuitable for use in large quantities. Moreover, the reaction devised by Ueda et al. presents a non-optimal yield for 2-(2-methyl-1,3-dioxolan-2-yl)-N'-phenylacetohydrazide (30%). Most importantly, when the inventors tried to reproduce said reaction with similar conditions and a naphthylhydrazine was used instead of the phenylhydrazine (see Example 26 below), they were unsuccessful in preparing the desired final intermediate in optimal isomeric purity. Adversely, an isomeric mixture (80:20) of 5-methyl-1-(naphthalen-2-yl)-1H-pyrazol-3-ol (desired isomer) and 3-methyl-1-(naphthalen-2-yl)-1H-pyrazol-5-ol (non-desired isomer) was obtained. This process does not avoid the distal nitrogen of the hydrazine from reacting with the ketone carbonyl of the ketoacetate, thereby generating by-products that make this route not interesting for industrial production.

As such, the inventors confronted with the problems on the control of the regioselectivity of the mentioned reaction, and trying to meet the need for an improved and industrially feasible process when compared to the ones proposed by WO2006021462, WO2007098953, WO2009130314, and Ueda et al., they have envisaged a regioselective process where the ketoacetate is replaced by a more advantageous reagent—the acid form—and have surprisingly found that said process not only works and results in an increased yield versus the prior art processes, but it also allows the industrial production of these intermediates with, most importantly, a high degree of isomeric purity.

SUMMARY OF THE INVENTION

The present invention relates to a process for the preparation of a compound of formula (V),

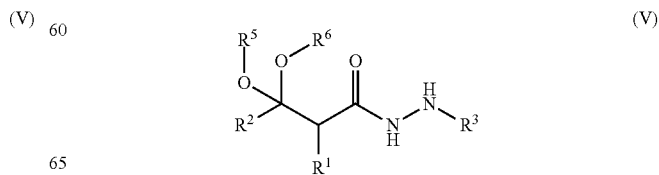

said process comprising the step of:

a1) coupling a compound of formula (II) with a compound of formula (IV) in a suitable solvent, in the presence of a coupling agent, and optionally in the presence of an activating agent of the coupling agent; or

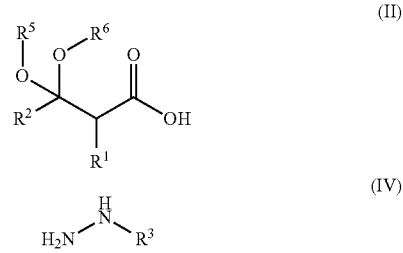

a2) converting a compound of formula (II) into a compound of formula (III) with an activating agent, and coupling said compound of formula (III) with a compound of formula (IV) in a suitable solvent,

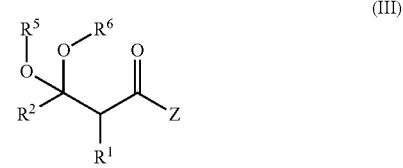

wherein in each of the compounds of formula (II), (III), (IV), and (V), where applicable, $R^1$ is hydrogen or $C_{1-6}$alkyl;

$R^2$ is hydrogen, $C_{1-6}$alkyl, or phenyl;

$R^3$ is naphthyl optionally substituted with one or two substituents selected from halo and $C_{1-6}$alkoxy;

$R^5$ and $R^6$ are, each independently, $C_{1-6}$alkyl, polyhalo$C_{1-6}$alkyl, —C(=O)—$C_{1-6}$alkyl, phenyl, benzyl optionally substituted with nitro; or together with the two oxygen atoms to which they are attached to, form a 4-7 membered heterocyclic ring optionally substituted with one substituent selected from halo, $C_{1-6}$alkyl, $C_{2-6}$alkenyl, polyhalo$C_{1-6}$alkyl, tri$C_{1-6}$alkylsilyl, di$C_{1-6}$alkylphenylsilyl, $C_{1-6}$alkyldiphenylsilyl, tri$C_{1-6}$alkylsilyl$C_{1-6}$alkyl, di$C_{1-6}$alkylphenylsilyl$C_{1-6}$alkyl, $C_{1-6}$alkyldiphenylsilyl$C_{1-6}$alkyl, phenyl optionally substituted with nitro or methoxy, and pyridyl; or the 4-7 membered heterocyclic ring is optionally substituted with two substituents selected from halo and $C_{1-6}$alkyl;

Z represents halo, —O—CO—$R^7$, or O—CO—O$R^7$; and $R^7$ is $C_{1-4}$alkyl, aryl, or benzyl.

The invention also relates to the process presented above, wherein the ketal or acetal group of the compound of formula (V) is further cleaved in a suitable solvent;

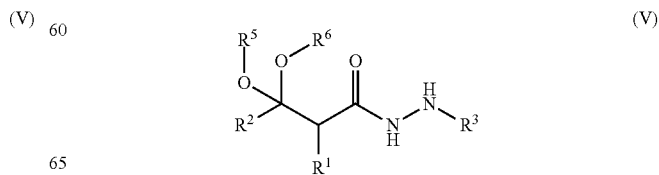

thereby forming a compound of formula (VI),

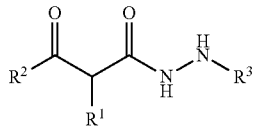

(VI)

and cyclization of the compound of formula (VI) is allowed, thereby obtaining a compound of formula (VII), a tautomer (VIIa), and salts thereof;

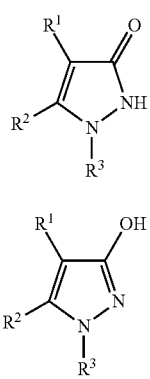

(VII)

(VIIa)

wherein in each of compounds of formula (V), (VI), (VII), and (VIIa), where applicable,
$R^1$, $R^2$, $R^3$, $R^5$, and $R^6$ are as defined above.

The above reactions may be performed in a one-pot fashion.

The invention further relates to compounds of formula (VI), (V), (III), (II), and (IIa), per se, the salts and stereoisomers thereof, and to the use of (VI), (V), (III), (II), (IIa), and (I), the salts and stereoisomers thereof, as intermediates in the preparation of a compound of formula (X), pharmaceutically acceptable salts, isomers, prodrugs, and solvates thereof.

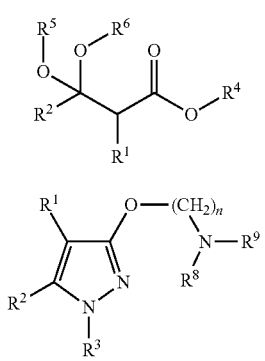

(I)

(X)

wherein in each of compounds of formula (I) and (X), where applicable,
$R^1$, $R^2$, $R^3$, $R^5$, and $R^6$ are as defined above and $R^4$, $R^8$, $R^9$, and n will be defined hereinafter.

DISCLOSURE OF THE INVENTION

The present invention relates to a process for the preparation of a compound of formula (V),

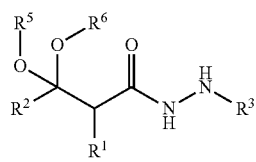

(V)

said process comprising the step of:
a1) coupling a compound of formula (II) with a compound of formula (IV) in a suitable solvent, in the presence of a coupling agent, and optionally in the presence of an activating agent of the coupling agent; or

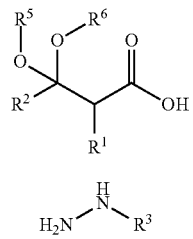

(II)

(IV)

a2) converting a compound of formula (II) into a compound of formula (III) with an activating agent, and coupling said compound of formula (III) with a compound of formula (IV) in a suitable solvent,

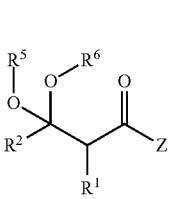

(III)

wherein in each of the compounds of formula (II), (III), (IV), and (V), where applicable,
$R^1$ is hydrogen or $C_{1-6}$alkyl;
$R^2$ is hydrogen, $C_{1-6}$alkyl, or phenyl;
$R^3$ is naphthyl optionally substituted with one or two substituents selected from halo and $C_{1-6}$alkoxy;
$R^5$ and $R^6$ are, each independently, $C_{1-6}$alkyl, polyhalo$C_{1-6}$alkyl, —C(=O)—$C_{1-6}$alkyl, phenyl, benzyl optionally substituted with nitro; or together with the two oxygen atoms to which they are attached to, form a 4-7 membered heterocyclic ring optionally substituted with one substituent selected from halo, $C_{1-6}$alkyl, $C_{2-6}$alkenyl, polyhalo$C_{1-6}$alkyl, tri$C_{1-6}$alkylsilyl, di$C_{1-6}$alkylphenylsilyl, $C_{1-6}$alkyldiphenylsilyl, tri$C_{1-6}$alkylsilyl$C_{1-6}$alkyl, di$C_{1-6}$alkylphenylsilyl$C_{1-6}$alkyl, $C_{1-6}$alkyldiphenylsilyl$C_{1-6}$alkyl, phenyl optionally substituted with nitro or methoxy, and pyridyl; or the 4-7 membered heterocyclic ring is optionally substituted with two substituents selected from halo and $C_{1-6}$alkyl;
Z represents halo, —O—CO—$R^7$, or O—CO—O$R^7$; and
$R^7$ is $C_{1-4}$alkyl, aryl, or benzyl.

As used hereinbefore or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the group defined for $C_{1-4}$alkyl and pentyl, hexyl, 2-methylbutyl, and the like.

The term $C_{2-6}$alkenyl as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_{2-6}$alkenyl is $C_{2-4}$alkenyl.

The term $C_{1-6}$alkoxy means $C_{1-6}$alkyloxy or a $C_{1-6}$alkyl ether radical, wherein the term $C_{1-6}$alkyl is as defined above. Examples of suitable alkyl ether radicals include methoxy, ethoxy, n-propoxy, isopropoxy, n-butoxy, iso-butoxy, sec-butoxy, tert-butoxy, hexanoxy and the like.

As used herein, the term halide refers to fluorine, chlorine, bromine, and iodine.

The term halo is generic to fluoro, chloro, bromo, and iodo.

The term polyhalo$C_{1-6}$alkyl as a group or part of a group, e.g. in polyhalo$C_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoro$C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-6}$alkyl, the halogen atoms may be the same or different.

The term naphthyl refers to naphth-1-yl or naphth-2-yl. The naphth-1-yl ring may be substituted, for example with one or two halo or $C_{1-6}$alkoxy in each of the positions 2, 3, 4, 5, 6, 7, and 8. The naphth-2-yl ring may be substituted, for example with one or two halo or $C_{1-6}$alkoxy in each of the positions 1, 3, 4, 5, 6, 7, and 8. In a preferred embodiment, the naphthyl ring is naphth-2-yl. In a preferred embodiment, the naphth-2-yl ring is unsubstituted. In another embodiment, the naphth-2-yl ring is substituted in positions 5, 6, or 7 by a $C_{1-6}$alkoxy group, preferably selected from methoxy, ethoxy, n-propoxy, and isopropoxy.

Aryl as a group or part of a group refers to single and multiple ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

It should be noted that the radical positions on any molecular moiety used in the definitions may be anywhere on such moiety as long as it is chemically stable.

Radicals used in the definitions of the variables include all possible isomers unless otherwise indicated. For instance pentyl includes 1-pentyl, 2-pentyl and 3-pentyl; piperidinyl includes 1-piperidinyl, 2-piperidinyl, 3-piperidinyl, or 4-piperidinyl.

When any variable occurs more than one time in any constituent, each definition is independent.

In each of the compounds of the present invention, $R^1$ is preferably selected from hydrogen, methyl, ethyl, propyl, and isopropyl. More preferably, $R^1$ is selected from hydrogen and methyl. Even more preferably $R^1$ is hydrogen.

In each of the compounds of the present invention, $R^2$ is preferably selected from hydrogen, methyl, ethyl, propyl, isopropyl, and phenyl. More preferably, $R^2$ is selected from hydrogen, methyl, isopropyl, and phenyl. Even more preferably $R^2$ is methyl.

Compound of formula (V) may be prepared by either of the processes presented in step a1) or step a2).

The coupling reactions of each of steps a1) and a2) are conducted according to the methods known by the skilled in the art in a suitable solvent. Such suitable solvent is usually of inert nature, such as halogenated hydrocarbons, e.g. dichloromethane, chloroform, dipolar aprotic solvents such as acetonitrile, dimethylformamide, dimethylacemide, ethers such as tetrahydrofuran, alcohols such as methanol, isopropanol, and the like, toluene, ethyl acetate, water, amongst other. In particular, solvents suitable for step a2) are dichloromethane and toluene.

The coupling reaction of step a1) is performed in the presence of a coupling agent according to the methods known by the skilled in the art. Such coupling agent may be preferably selected from (7-azabenzotriazol-1-yloxy)tripyrrolidinophosphonium hexafluorophosphate (PyAOP), (benzotriazol-1-yloxy)tripyrrolidinophosphonium hexafluorophosphate (PyBOP®), (benzotriazol-1-yloxy)tris (dimethylamino) phosphonium hexafluorophosphate (BOP, Castro's reagent), 1-(3-dimethylaminopropyl)-3-ethylcarbodiimide (EDC), N-(3-dimethylaminopropyl)-N'-ethylcarbodiimide hydrochloride (EDC hydrochloride, EDAC), 1,1'-carbonyl-di-(1,2,4-triazole) (CDT), 1,3-di-p-tolylcarbodiimide, 1-[3-(dimethylamino)propyl]-3-ethylcarbodiimide methiodide (EDC methiodide), 1-isobutyloxycarbonyl-2-isobutyloxy-1,2-dihydroquinoline (IIDQ), 1-tert-butyl-3-ethylcarbodiimide (BEC), 2-(1H-benzotriazol-1-yl)-N,N,N',N'-tetramethyluronium tetrafluoroborate (TBTU), 2-chloro-1,3-dimethylimidazolidinium chloride (DMC), 2-chloro-1,3-dimethylimidazolidinium hexafluorophosphate (CIP), 2-chloro-1,3-dimethylimidazolidinium tetrafluoroborate (CIB), 2-chloro-1-methylpyridinium iodide, 2-chloro-4,6-dimethoxy-1,3,5-triazine (CDMT), 2-ethoxy-1-ethoxycarbonyl-1,2-dihydroquinoline (EEDQ), 2-fluoro-1,3-dimethylimidazolidinium hexafluorophosphate (DFIH), 3-(diethoxyphosphoryloxy)-1,2,3-benzotriazin-4 (3H)-one (DEPBT), 4-(4,6-dimethoxy-1,3,5-triazin-2-yl)-4-methyl-morpholinium chloride (DMTMM), bromotripyrrolidinophosphonium hexafluorophosphate (PyBroP®), bromotris (dimethylamino)phosphonium hexafluorophosphate (BroP), chlorotripyrrolidinophosphonium hexafluorophosphate (PyCloP), diphenyl phosphoryl azide (DPPA), dipyrrolidino(N-succinimidyloxy)carbenium (HSPyU), N,N,N',N'-tetramethyl-O—(N-succinimidyl)uronium hexafluorophosphate (HSTU), N,N,N',N'-tetramethyl-O—(N-succinimidyl)uronium tetrafluoroborate (TSTU), N,N'-carbonyl-diimidazole (CDI), N,N'-dicyclohexylcarbodiimide (DCC), N,N'-diisopropylcarbodiimide (DIC), N,N'-di-tert-butylcarbodiimide, N-cyclohexyl-N'-(2-morpholinoethyl)carbodiimide methoptoluenesulfonate (CMC), O-(2-oxo-1(2H)pyridyl)-N,N,N',N'-tetramethyluronium tetrafluoroborate (TPTU), O-(3,4-dihydro-4-oxo-1,2,3-benzotriazin-3-yl)-N,N,N',N'-tetramethyluronium tetrafluoroborate (TDBTU), O-(6-chlorobenzotriazol-1-yl)-N,N,N',N'-tetramethyluronium (TCTU), O-(6-chlorobenzotriazol-1-yl)-N,N,N',N'-tetramethyluronium hexafluorophosphate (HCTU), O-(7-azabenzotriazol-1-yl)-N,N,N',N'-tetramethyluronium hexafluorophosphate (HATU), O-(benzotriazol-1-yl)-N,N,N',N'-bis(tetramethylene)uranium hexafluorophosphate (HBPyU), O-(benzotriazol-1-yl)-N,N,N',N'-tetramethyluronium hexafluorophosphate (HBTU), O-[(ethoxycarbonyl)cyanomethylenamino]-N,N,N',N'-tetramethyluronium hexafluorophosphate (HOTU), O-[(ethoxycarbonyl)cyanomethylenamino]-N,N,N',N'-tetramethyluronium tetrafluoroborate (TOTU), O-benzotriazol-1-yl-N,N,N',N'-bis(pentamethylene)uranium hexafluorophosphate (HBPipU), oxalic acid diimidazolide, propylphosphonic anhydride solution, S-(1-oxido-2-pyridyl)-N,N,N',N'-tetramethylthiuronium tetrafluoroborate (TOTT), fluoro-N,N,N',N'-tetramethylformamidinium hexafluorophosphate (TFFH), and fluoro-N,N,N',N'-bis(tetramethylene)formamidinium hexafluorophosphate (BTFFH).

Preferably, the coupling agent in step a1) is a carbodiimide, more preferably, dicyclohexylcarbodiimide (DCC), diisopropylcarbodiimide (DIC), or N-ethyl-N'-[(3-dimethylamino)propyl]carbodiimide (EDC).

In many instances, the coupling reaction of step a1) can be enhanced by the addition of an activating agent of the coupling agent that can be conveniently selected from 1-hydroxybenzotriazole (HOBt) and 4-dimethylaminopyridine (4-DMAP).

The reaction temperature of coupling reactions of steps a1) or a2) may range between 0° C. and 50° C. and the reaction time may range between 15 min and 24 h.

According to step a2) of the process for the preparation of the compound of formula (V), the compound of formula (II) may be converted into an activated form, i.e. the compound of formula (III), with the use of an activating agent according to the methods known by the skilled in the art. Such activating agent may be preferably selected from a halogenating agent, $C_{1-4}$alkyl acid halide, aryl acid halide, benzyl acid halide, $C_{1-4}$alkyl haloformate, aryl haloformate, and benzyl haloformate.

Examples of halogenating agents that may be used include, but are not limited to, inorganic acid halides, cyanuric chloride, thionyl chloride, $PCl_5$, $POCl_3$, Vilsmeier reagent, Golds reagent, chlorinated heterocycles, and combinations of halogenating agents such as halogens, $CCl_4$, $C_2Cl_6$, or other alkyl halides with reducing agents such as triaryl or trialkyl phosphines or phosphites or a hydrogen halide in the presence of a dehydrating agent. Examples of $C_{1-4}$alkyl acid halides include acetyl chloride, propionyl chloride, butanoyl chloride, and the like. Examples of aryl acid halides include phthaloyl chloride, isophthaloyl chloride, and terphthaloyl chloride. Examples of benzyl acid halides include benzoyl chloride, benzoyl fluoride, benzoyl bromide. Examples of $C_{1-4}$alkyl haloformate include methyl chloroformate, ethyl chloroformate, isopropyl chloroformate, and the like. Examples of aryl haloformate include phenyl chloroformate, phenyl fluoroformate, and the like. Examples of benzyl haloformates include benzyl chloroformate, benzyl fluoroformate, and the like. Other examples of halogenating agents include 1-chloro-N,N-2-trimethyl-1-propenylamine, chloro-N,N,N',N'-bis(tetramethylene)formamidinium tetrafluoroborate (PyClU), and chloro-N,N,N',N'-tetramethylformamidinium hexafluorophosphate.

In one embodiment of the present invention, when compound of formula (II) is activated as a compound of formula (III), in which Z is halo, it may be convenient to add a base to the reaction mixture in order to neutralize a possible in situ formed acid, such as hydrochloric acid.

Another embodiment of the present invention relates to the process presented above, wherein the ketal or acetal group of compound of formula (V) is further cleaved in a suitable solvent;

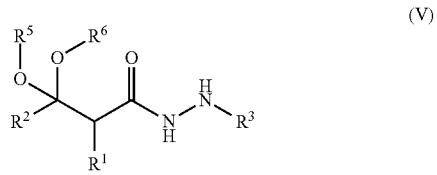

thereby forming compound of formula (VI),

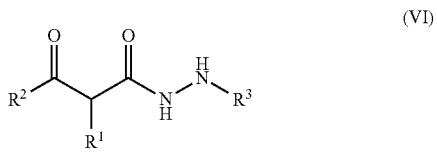

and cyclization of compound of formula (VI) is allowed, thereby obtaining compound of formula (VII), a tautomer (VIIa), and salts thereof;

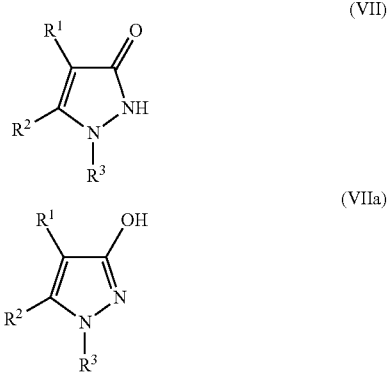

wherein in each of compounds of formula (V), (VI), (VII), and (VIIa), where applicable,
$R^1$, $R^2$, $R^3$, $R^5$, and $R^6$ are as defined above.

The ketal group refers to the functional group constituted by the carbon bonded to the —$OR^5$ and —$OR^6$ groups, and where $R^2$ is not hydrogen. The acetal group refers to the functional group constituted by the carbon bonded to the —$OR^5$ and —$OR^6$ groups, and where $R^2$ is hydrogen.

The term salt as mentioned herein is meant to comprise any stable salts, which the compounds described herein, such as the intermediates of formula (IV), (VII), or (VIIa), are able to form. Preferred are the pharmaceutically acceptable salts, which are the non-toxic salt forms. Salts that are not pharmaceutically acceptable are also embraced in the scope of the present invention, since they refer to intermediates that are useful in the preparation of compounds with pharmacological activity. The salts can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propane-tricarboxylic, methanesulfonic, ethanesulfonic, benzenesulfonic, 4-methylbenzene-sulfonic, cyclohexanesulfamic, 2-hydroxybenzoic, 4-amino-2-hydroxybenzoic and the like acids. Conversely the salt form can be converted by treatment with alkali into the free base form. The term salts is also meant to include the hydrates or solvates which the compounds of formula (VII) and (VIIa) are able to form, including, e.g. the alcoholates such as methanolates or ethanolates.

The phrase "pharmaceutically acceptable" refers to molecular entities and compositions that do not produce adverse, allergic, or other untoward reactions when administered to an animal or a human.

The cleavage of the ketal or acetal group of compound of formula (V) is a common procedure that can be carried out by the methods generally known to the skilled in the art. One usual procedure to cleave ketal or acetal groups is acidic treatment. The acidic treatment refers to the use of an acid in a suitable solvent such as an aqueous medium, an organic solvent, or mixtures thereof. The organic solvent may be selected from water-miscible solvents such as acetonitrile, dimethylformamide, alcohols such as methanol, and the like.

Other possible procedures for the cleavage of the ketal or acetal group in compound of formula (V) are described in the following paragraphs. These procedures are known in the art, for example they are described in *Greene's Protective Groups in Organic Synthesis*, by Peter G. M. Wuts and Theodora W. Greene.

Where $R^5$ and $R^6$ are, each independently, $C_{1-6}$alkyl or phenyl, cleavage of the ketal/acetal group may be performed with hydrochloric acid and a mixture of water and methanol; with 2,2,2-trifluoroacetic acid in a mixture of chloroform and water at a cool temperature, such as 0° C.; with p-toluenesulfonic acid in acetone; with silicon dioxide and oxalic or sulfuric acid; with trimethylsilyliodide in dichloromethane; with titanium tetrachloride and lithium iodide in diethylether; with lithium tetrafluoroborate in acetonitrile; with formic acid in pentane; with formic acid in tetrahydrofuran and water; with Amberlyst-15 in acetone and water; with hydrogen peroxide and trichloroacetic acid in dichloromethane and t-butanol followed by the addition of dimethyl sulfide; with trifluoroacetic acid and sodium bicarbonate; with acetic acid in water; with oxalic acid in tetrahydrofuran and water; with trifluoroborane ethoxyethane ($BF_3.Et_2O$), tetraethylammonium iodide, in trichloromethane; with 10% water, silica gel, dichloromethane; with dimethylsulfoxide, water, dioxane, and heating to reflux; with diodosilane ($SiH_2I_2$) in acetonitrile at cool temperatures (approx. −40° C.); with molybdenum acetylacetonate ($Mo_2(acac)_2$) in acetonitrile; with acetyl chloride, samarium (III) chloride ($SmCl_3$) in pentane; with stannous chloride dehydrate, $C_{60}$, and dichloromethane; amongst other.

Where $R^5$ and $R^6$ are, each independently, polyhalo$C_{1-6}$ alkyl, cleavage of the ketal/acetal group may be performed with zinc in ethyl acetate or tetrahydrofuran, at reflux temperature.

Where $R^5$ and $R^6$ are, each independently, benzyl, cleavage of the ketal/acetal group may be performed with palladium on carbon, hydrogen, and methanol as solvent.

Where $R^5$ and $R^6$ are, each independently, 2-nitrobenzyl, cleavage of the ketal/acetal group may be performed with photolysis at 350 nm Where $R^5$ and $R^6$ are, each independently, acetyl, cleavage of the ketal/acetal group may be performed with sodium hydroxide or potassium carbonate, in tetrahydrofuran, water, or methanol; with alumina at approx. 35° C.; with potassium 3-dimethylaminophenoxide in tetrahydrofuran at 0° C.; with expansive graphite, dichloromethane or benzene, at reflux temperature; with CAN, silica gel, in dichloromethane; with montmorillonite clay K-10 or KSF in dichloromethane at reflux temperature; or with the use of enzymes for the hydrolysis of the acylals.

Where $R^5$ and $R^6$, together with the two oxygen atoms to which they are attached to, form a 1,3-dioxane, 1,3-dioxolane, 4-methyl-1,3-dioxolane, cleavage of the ketal/acetal group may be performed with pyridinium tosylate (PPTS), acetone, water, and heat; with acetone and p-toluenesulfonic acid monohydrate (TsOH); with acetone, water, PPTS, at reflux temperature; with hydrochloric acid and a mixture of water and methanol; with 5% HCl in tetrahydrofuran; with 1 M HCl in tetrahydrofuran and warming the reaction mixture from 0° C. to 25° C.; with 80% acetic acid at around 65° C.; with wet magnesium sulfate and benzene; with perchloric acid in dichloromethane and warming the reaction mixture from 0° C. to 25° C.; amongst other methods.

Where $R^5$ and $R^6$, together with the two oxygen atoms to which they are attached to, form a 5-methylene-1,3-dioxane, cleavage of the ketal/acetal group may be performed according to the procedures described by R. J. Corey and J. W. Suggs, *Tetrahedron Lett.*, 3775 (1975), or by H. Frauenrath and M. Kaulard, Synlett, 517 (1994).

Where $R^5$ and $R^6$, together with the two oxygen atoms to which they are attached to, form a 5,5-dibromo-1,3-dioxane, cleavage of the ketal/acetal group may be performed with Zn—Ag, in tetrahydrofuran and acetic acid.

Where $R^5$ and $R^6$, together with the two oxygen atoms to which they are attached to, form a 542'-pyridyl)-1,3-dioxane, cleavage of the ketal/acetal group may be performed according to the procedure described by A. R. Katritzky, W.-Q. Fan, and Q.-L. Li, *Tetrahedron Lett.*, 28, 1195 (1987).

Where $R^5$ and $R^6$, together with the two oxygen atoms to which they are attached to, form a 5-trimethylsilyl-1,3-dioxane, cleavage of the ketal/acetal group may be performed with trifluoroborane ethoxyethane ($BF_3.Et_2O$) in tetrahydrofuran; or with lithium tetrafluoroborate in tetrahydrofuran at around 65° C.

Where $R^5$ and $R^6$, together with the two oxygen atoms to which they are attached to, form a 4-bromomethyl-1,3-dioxolane, cleavage of the ketal/acetal group may be performed according to the method described by E. J. Corey and R. A. Ruden, *J. Org. Chem.*, 38, 834 (1973).

Where $R^5$ and $R^6$, together with the two oxygen atoms to which they are attached to, form a 4-(3-butenyl-1,3-dioxolane, cleavage of the ketal/acetal group may be performed according to the method described by Z. Wu, D. R. Mootoo, and B. Fraser-Reid, *Tetrahedron Lett.*, 29, 6549 (1988).

Where $R^5$ and $R^6$, together with the two oxygen atoms to which they are attached to, form a 4-phenyl-1,3-dioxolane, cleavage of the ketal/acetal group may be performed with electrolysis: Lithium perchlorate, water, pyridine, acetonitrile, N-hydroxyphthalimide; 0.85 V SCE; or with palladium on carbon and hydrogen.

Where $R^5$ and $R^6$, together with the two oxygen atoms to which they are attached to, form a 4-(4-methoxyphenyl)-1,3-dioxolane, cleavage of the ketal/acetal group may be performed according to the method described by C. E. McDonald, L. E. Nice, and K. E. Kennedy, *Tetrahedron Lett.*, 35, 57 (1994).

Where $R^5$ and $R^6$, together with the two oxygen atoms to which they are attached to, form a 4-(2-nitrophenyl)-1,3-dioxolane, cleavage of the ketal/acetal group may be performed by irradiation at 350 nm, with benzene.

Where $R^5$ and $R^6$, together with the two oxygen atoms to which they are attached to, form a 4-trimethylsilylmethyl-1,3-dioxolane, cleavage of the ketal/acetal group may be performed according to the method described by B. M. Lillie and M. A. Avery, *Tetrahedron Lett.*, 35, 969 (1994).

Once the ketal or acetal group of compound of formula (V) is cleaved, the resulting compound of formula (VI) cyclises in the same reaction mixture. Cyclization usually occurs spontaneously. Alternatively, it may be induced or accelerated by heating or other methods known by the skilled in the art. In a preferred embodiment, the cyclisation is performed under a temperature between room temperature and reflux temperature, preferably at a temperature between 50° C. and reflux temperature, more preferably at reflux temperature.

In one embodiment of the present invention, the preparation of compounds of formula (V), (VI), (VII), a tautomer (VIIa), and salts thereof, occurs in a one-pot procedure, which is advantageous in an industrial production. As such, one embodiment of the present invention relates to a process for the preparation of a compound of formula (VII), a tautomer (VIIa), and salts thereof, as defined in claim 2, said process comprising the steps of:

a1) coupling a compound of formula (II) with a compound of formula (IV) in a suitable solvent, in the presence of a coupling agent, and optionally in the presence of an activating agent of the coupling agent,

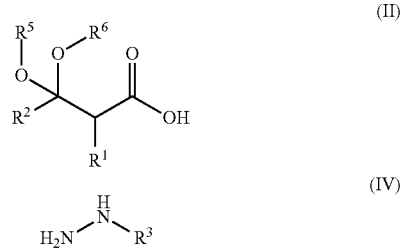

or a2) converting a compound of formula (II) into a compound of formula (III) with an activating agent, and coupling said compound of formula (III) with a compound of formula (IV) in a suitable solvent.

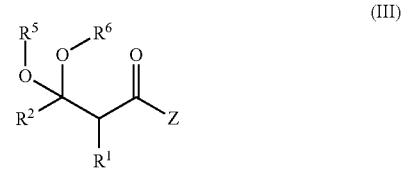

thereby obtaining compound of formula (V),

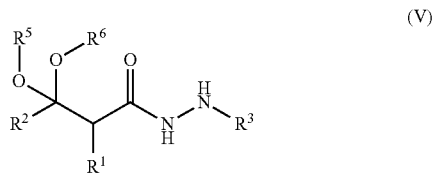

followed by the cleavage, in the same reaction mixture, of the ketal or acetal group of the compound of formula (V) in a suitable solvent, thereby forming compound of formula (VI),

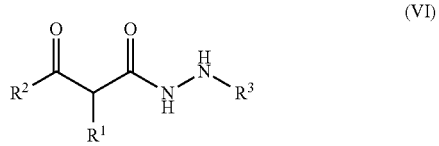

and allowing cyclization of the compound of formula (VI), thereby obtaining a compound of formula (VII), a tautomer (VIIa), and salts thereof; wherein in each of compounds of formula (V), (VI), (VII), and (VIIa), where applicable, $R^1$, $R^2$, $R^3$, $R^5$, $R^6$, $R^7$, and Z are as defined above.

In the reactions mentioned above, in particular in steps a1) or a2), the compound of formula (IV) may be added as such as a base free form, or as a salt thereof. In the case where the compound of formula (IV) is added in salt form, the free base form is consequently obtained by reacting said salt with an alkali base. Such reaction may be performed in the same reaction mixture comprising compounds of formula (II) or (III), as the case may be. Typical salts that compound of formula (IV) may form have already been mentioned above. A preferred salt is chlorohydrate.

Interesting compounds of formula (IV) include the following:

2-naphthylhydrazine (CAS Registry Number: 2243-57-4), which may be obtained from BetaPharma Shanghai, HC Scientific Resources, Bidragon Pharmservice, ARVI, Aurora Screening, and many others;

2-naphthalenyl hydrazine hydrochloride (CAS Registry Number: 2243-58-5), which may be obtained from Advanced Technology, Allichem, AK Scientific, Chem-Pacific, HC Scientific Resources, Bidragon Pharmservice, and many others.

In one embodiment of the present invention, the compound of formula (II) may be prepared by cleaving $R^4$ from a compound of formula (I)

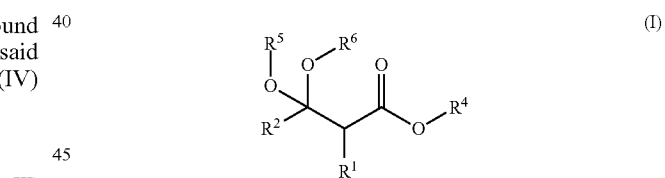

wherein in compound of formula (I),
$R^1$, $R^2$, $R^5$, and $R^6$ are as defined above; and
$R^4$ is $C_{1-6}$alkyl, aryl, or benzyl.

Cleavage of the substituent $R^4$ from compound of formula (I) is carried out according to the several methods known by the skilled in the art for cleaving esters.

A common method for cleaving esters is hydrolysis. Examples of hydrolysis procedures include the addition of aqueous solutions of strong acids, such as, for example, HCl or $H_2SO_4$, or strong bases, such as, for example, NaOH, KOH or LiOH. The hydrolysis reaction can be carried out in an organic solvent, in water, in mixtures of organic solvents, or in mixtures of organic solvents with water. Examples of organic solvents include ethers, such as diethyl ether, butyl methyl ether, dioxane, tetrahydrofuran, glycol dimethyl ether or diethylene glycol dimethyl ether, or hydrocarbons such as benzene, toluene, xylene or petroleum ether, or alcohols, such as methanol or ethanol, or halogenated hydrocarbons, such as carbon tetrachloride, chloromethane or dichloromethane. In a preferred embodiment of the invention, the solvent is a mixture of water and methanol or dioxane. The reaction can generally be carried out in a temperature range of from −20° C. to 90° C., preferably of from 0° C. to 90° C. The reaction can be carried out under atmospheric pressure, elevated or reduced pressure (for example in a range of from 0.5 to 5 bar). In general, the reaction is carried out under atmospheric pressure.

Interesting compounds of formula (I) include the following:
- ethyl 2-(2,4-dimethyl-1,3-dioxolan-2-yl)acetate (CAS Registry Number: 6290-17-1), which is available from 3B Scientific Corporation, Takasago International Corp, Amfinecom Inc., and Bepharm Ltd., amongst other.
- ethyl 3,3-diethoxypropanoate (CAS Registry Number: 10601-80-6), which is available from APAC Pharmaceutical Waterstone Technology Zelinsky Screening, TCI Organic Chemicals, Aldrich, and many others.

It is evident that in the foregoing and in the following reactions, the reaction products may be isolated from the reaction medium and, if necessary, further purified according to methodologies generally known in the art such as extraction, crystallization and chromatography.

As such, one embodiment of the present invention refers to a compound of formula (VI), per se, a salt, or stereoisomer thereof,

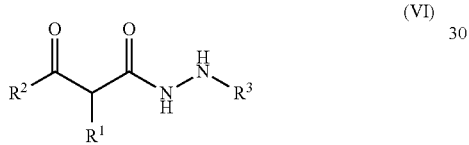

wherein,
$R^1$ is hydrogen or $C_{1-6}$alkyl;
$R^2$ is hydrogen, $C_{1-6}$alkyl, or phenyl; and
$R^3$ is naphthyl optionally substituted with one or two substituents selected from halo and $C_{1-6}$alkoxy.

An interesting group of compounds are those compounds of formula (VI) where one or more of the following restrictions apply:
$R^1$ is hydrogen;
$R^2$ is $C_{1-6}$alkyl; and/or
$R^3$ is naphthyl optionally substituted with one or two substituents selected from halo and $C_{1-6}$alkoxy.

Another interesting group of compounds are those compounds of formula (VI) where one or more of the following restrictions apply:
$R^1$ is hydrogen;
$R^2$ is methyl; and/or
$R^3$ is napht-2-yl.

Another embodiment of the present invention refers to a compound of formula (V), per se, a salt, or stereoisomer thereof,

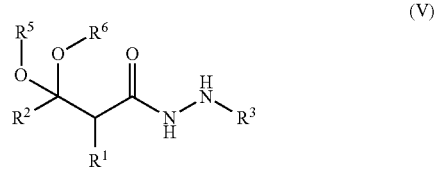

wherein,
$R^1$ is hydrogen or $C_{1-6}$alkyl;
$R^2$ is hydrogen, $C_{1-6}$alkyl, or phenyl;
$R^3$ is naphthyl optionally substituted with one or two substituents selected from halo and $C_{1-6}$alkoxy; and
$R^5$ and $R^6$ are, each independently, $C_{1-6}$alkyl, polyhalo$C_{1-6}$alkyl, —C(═O)—$C_{1-6}$alkyl, phenyl, benzyl optionally substituted with nitro; or together with the two oxygen atoms to which they are attached to, form a 4-7 membered heterocyclic ring optionally substituted with one substituent selected from halo, $C_{1-6}$alkyl, $C_{2-6}$alkenyl, polyhalo$C_{1-6}$alkyl, tri$C_{1-6}$alkylsilyl, di$C_{1-6}$alkylphenylsilyl, $C_{1-6}$alkyldiphenylsilyl, tri$C_{1-6}$alkylsilyl$C_{1-6}$alkyl, di$C_{1-6}$alkylphenylsilyl$C_{1-6}$alkyl, $C_{1-6}$alkyldiphenylsilyl$C_{1-6}$alkyl, phenyl optionally substituted with nitro or methoxy, and pyridyl; or the 4-7 membered heterocyclic ring is optionally substituted with two substituents selected from halo and $C_{1-6}$alkyl.

Another interesting group of compounds are those compounds of formula (V) where one or more of the following restrictions apply:
$R^1$ is hydrogen;
$R^2$ is hydrogen or $C_{1-6}$alkyl;
$R^3$ is naphthyl optionally substituted with one or two substituents selected from halo and $C_{1-6}$alkoxy; and/or
$R^5$ and $R^6$ are, each independently, $C_{1-6}$alkyl; or together with the two oxygen atoms to which they are attached to, form a 4-7 membered heterocyclic ring optionally substituted with one substituent selected from halo, $C_{1-6}$alkyl, $C_{2-6}$alkenyl, halo$C_{1-6}$alkyl, trimethylsilyl, trimethylsilylmethyl, phenyl, 2-nitrophenyl, 4-methoxyphenyl, 2-pyridyl; or the 4-7 membered heterocyclic ring is optionally substituted with two substituents selected from halo and $C_{1-6}$alkyl.

Another interesting group of compounds are those compounds of formula (V) where one or more of the following restrictions apply:
$R^1$ is hydrogen;
$R^2$ is methyl;
$R^3$ is napht-2-yl; and/or
$R^5$ and $R^6$ are together with the two oxygen atoms to which they are attached to, form a 5 membered heterocyclic ring substituted with one $C_{1-6}$alkyl.

Another embodiment of the present invention refers to a compound of formula (III), per se, a salt, or stereoisomer thereof,

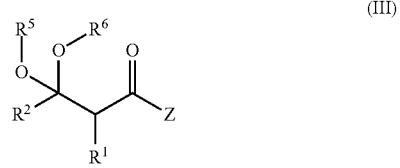

wherein,
$R^1$ is hydrogen or $C_{1-6}$alkyl;
$R^2$ is hydrogen, $C_{1-6}$alkyl, or phenyl;
$R^5$ and $R^6$ are, each independently, ethyl, butyl, or together with the two oxygen atoms to which they are attached to, form a 4-7 membered heterocyclic ring substituted with one or more substituents selected from halo, $C_{1-6}$alkyl, $C_{2-6}$alkenyl, polyhalo$C_{1-6}$alkyl, tri$C_{1-6}$alkylsilyl, di$C_{1-6}$alkylphenylsilyl, $C_{1-6}$alkyldiphenylsilyl, tri$C_{1-6}$alkylsilyl$C_{1-6}$alkyl, di$C_{1-6}$alkylphenylsilyl$C_{1-6}$alkyl, $C_{1-6}$alkyldiphenylsilyl$C_{1-6}$alkyl, phenyl optionally substituted with nitro or methoxy, and pyridyl; or the 4-7 membered heterocyclic ring is substituted with two substituents selected from halo and $C_{1-6}$alkyl; and/or
Z represents halo, —O—CO—$R^7$, or O—CO—O$R^7$; and $R^7$ is $C_{1-4}$alkyl, aryl, or benzyl.

Another interesting group of compounds are those compounds of formula (III) where one or more of the following restrictions apply:
$R^1$ is hydrogen;
$R^2$ is hydrogen or $C_{1-6}$alkyl;
$R^5$ and $R^6$ are, each independently, ethyl, butyl, or together with the two oxygen atoms to which they are attached to, form a 5 membered heterocyclic ring substituted with one substituent selected from halo, $C_{1-6}$alkyl, $C_{2-6}$alkenyl, polyhalo$C_{1-6}$alkyl; and/or
Z represents halo, —O—CO—$R^7$, or O—CO—O$R^7$; and $R^7$ is $C_{1-4}$alkyl.

Another interesting group of compounds are those compounds of formula (III) where one or more of the following restrictions apply:
$R^1$ is hydrogen;
$R^2$ is methyl;
$R^5$ and $R^6$ together with the two oxygen atoms to which they are attached to, form a 5 membered heterocyclic ring substituted with one substituent selected from halo, $C_{1-6}$alkyl, $C_{2-6}$alkenyl, polyhalo$C_{1-6}$alkyl; and/or
Z represents halo, —O—CO—$R^7$, or O—CO—O$R^7$; and $R^7$ is $C_{1-4}$alkyl.

Further interesting compounds are the following compounds embraced by formula (III):

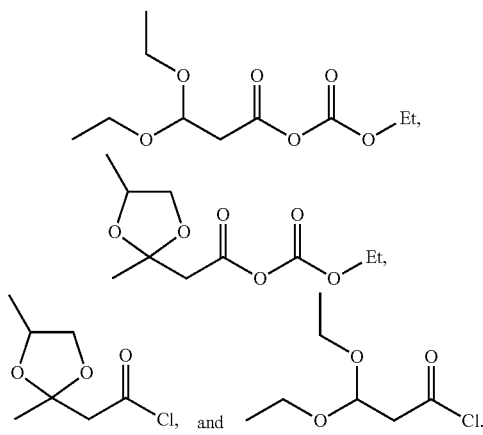

Another embodiment of the present invention refers to a compound of formula (II), per se, a salt, or stereoisomer thereof,

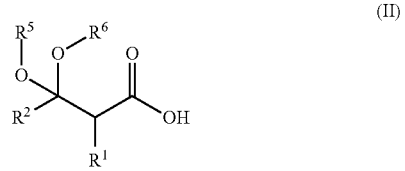

wherein
$R^1$ is hydrogen;
$R^2$ is methyl;

$R^5$ and $R^6$ are, each independently, $C_{3-7}$alkyl; or together with the two oxygen atoms to which they are attached to, form a 4-7 membered heterocyclic ring substituted with one substituent selected from halo, $C_{1-6}$alkyl, $C_{2-6}$alkenyl, polyhalo$C_{1-6}$alkyl, tri$C_{1-6}$alkylsilyl, di$C_{1-6}$alkylphenylsilyl, $C_{1-6}$alkyldiphenylsilyl, tri$C_{1-6}$alkylsilyl$C_{1-6}$alkyl, di$C_{1-6}$alkylphenylsilyl$C_{1-6}$alkyl, $C_{1-6}$alkyldiphenylsilyl$C_{1-6}$alkyl, phenyl optionally substituted with nitro or methoxy, and pyridyl; or the 4-7 membered heterocyclic ring is substituted with one halo and one $C_{1-6}$alkyl.

Another embodiment of the present invention refers to the following compound of formula (IIa), per se, a salt, or stereoisomer thereof.

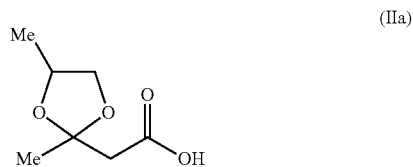 [SMILES: CC1COC(C)(CC(=O)O)O1]

Compounds of formula (I), (II), (IIa), (III), (V), and (VI) may have at least one center of chirality (indicated below with an asterisk) and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I), (II), (IIa), (III), (V), and (VI) may possess.

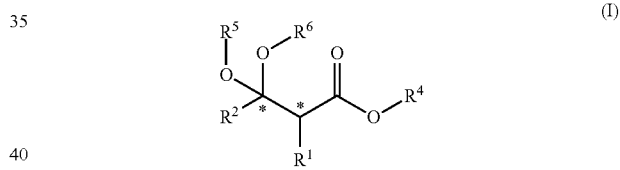

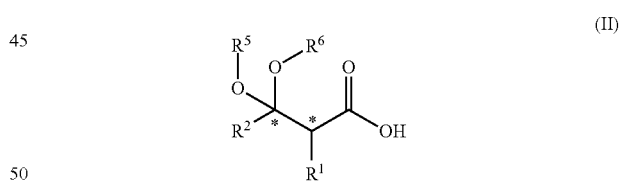

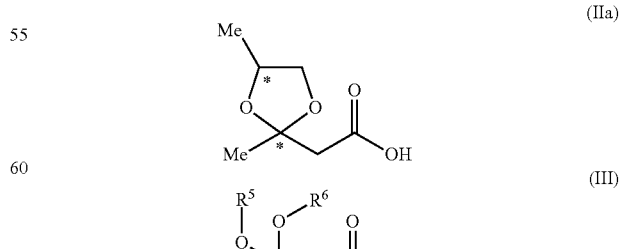

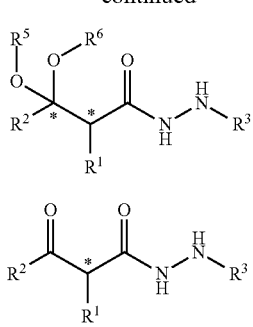

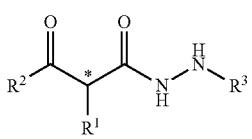

In each of the compounds depicted above, the carbon atom substituted with $R^1$ becomes a chiral center when $R^1$ is $C_{1-6}$alkyl.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compounds may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i e minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific processes of preparation. These processes will advantageously employ enantiomerically pure starting materials.

In the above-mentioned respective reactions, each of the obtained compounds, when necessary, can be collected from the reaction mixture according to the processes known in the art. For example, when insoluble materials are present, the desired compound can be obtained—after removing the insoluble materials by filtration—by removing the solvent, e.g. by removing the solvent under reduced pressure, and/or by adding water to the residue and extracting the mixture with a water-immiscible organic solvent such as ethyl acetate, etc. Optionally, the desired compound can be obtained after drying over anhydrous sodium sulfate, for instance, and further, if necessary, by purifying with any conventional process, such as recrystallization, column chromatography, or other techniques.

Examples of specific compounds of formula (VII) or (VIIa) in accordance with the invention include those compounds referred to in the Examples below, and the salts thereof.

The different compounds encompassed by formulae (VII) or (VIIa) may be converted into each other following art-known functional group transformation reactions. Suitably, they are obtained with starting materials, i.e. compounds of formula (I) and (IV) already embracing the desired substituents $R^1$, $R^2$, or $R^3$.

The compounds of formula of the present invention may be converted to the corresponding N-oxide forms following art-known procedures for converting a trivalent nitrogen into its N-oxide form. The N-oxide forms of the present compounds are meant to comprise the compounds of formula (VII) or (VIIa) wherein one or several nitrogen atoms are oxidized to the so-called N-oxide. Said N-oxidation reaction may generally be carried out by reacting compound of formula (VII) or (VIIa) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Due to their favorable processability properties, as will be apparent from the examples, the compounds of the present invention are useful as intermediates in the preparation of a compound of formula (X) as defined above. In general, the compounds of the present invention are useful in the preparation of a compound of formula (X), pharmaceutically acceptable salts, isomers, prodrugs, and solvates thereof, which has pharmacological activity against the sigma receptor—a cell surface receptor of the central nervous system, which is said to be related to the dysphoric, hallucinogenic and cardiac stimulant effects of opioids.

As such, one embodiment of the present invention refers to the use of compounds of formula (VII), a tautomer (VIIa), and salts thereof, as intermediates in the preparation of a compound of formula (X), pharmaceutically acceptable salts, isomers, prodrugs, and solvates thereof, said preparation according to the procedure or steps described herein,

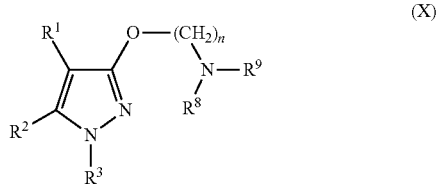

wherein, $R^1$, $R^2$, and $R^3$ are as defined above;

n is 2, 3, or 4; and $R^8$ and $R^9$ are, each independently, $C_{1-6}$alkyl, $C_{1-6}$alkoxy$C_{1-6}$alkyl, benzyl, or together with the nitrogen atom to which they are attached to, form a morpholinyl optionally substituted with $C_{1-6}$alkyl; thiomorpholinyl; piperazinyl optionally substituted with $C_{1-6}$alkyl, $C_{1-6}$alkylcarbonyl, or $C_{1-6}$alkoxycarbonyl; piperidinyl optionally substituted with $C_{1-6}$alkylcarbonyl, phenyl, or 3H-imidazo[4,5-b]pyridinyl; pyrrolidinyl optionally substituted with amino or $C_{1-6}$alkylcarbonylamino; pirazolinyl; 1,2,3,4-tetrahydroisoquinolinyl; or 3H-imidazo[4,5-b]pyridinyl.

Another embodiment of the present invention refers to the use of any one of compounds of formula (VI), (V), (III), (II), (IIa), and (I), a salt, or stereoisomer thereof, each independently, as intermediates in the preparation of a compound of formula (X), pharmaceutically acceptable salts, isomers, prodrugs, and solvates thereof, as referred to herein above.

The term 3H-imidazo[4,5-b]pyridinyl refers to the following moiety:

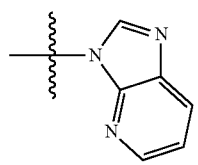 [SMILES: *n1cnc2cccnc21]

The term 1,2,3,4-tetrahydroisoquinolinyl refers to the following moiety:

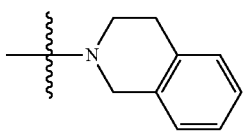 [SMILES: *N1CCc2ccccc2C1]

The term "prodrug" as used throughout this text means the pharmacologically acceptable derivatives such as esters, amides and phosphates, such that the resulting in vivo biotransformation product of the derivative is the active drug as defined in the compounds of formula (X). The reference by Goodman and Gilman (The Pharmacological Basis of Therapeutics, 8th ed, McGraw-1-Till, hit. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

The term "solvate", when referring to compounds of formula (X), refers to those crystal forms of the compounds of formula (X) that contain either stoichiometric or non-stoichiometric amounts of solvent. Since water is a solvent, solvates also include hydrates. The term "pseudopolymorph" is synonym to solvate since it applies to polymorphic crystalline forms that have solvent molecules incorporated in their lattice structures. Examples of solvates are hydrates and alcoholates such as methanolates or ethanolates.

The following specific examples are provided to further illustrate the invention and various preferred embodiments.

EXAMPLES

Synthesis of Compounds of Formula (II)

As shown in examples 1 and 2, two different compounds of formula (II) were synthesized: 2-(2,4-dimethyl-1,3-dioxolan-2-yl)acetic acid [i.e. compound (IIa)], which was used in the subsequent reactions, and 3,3-diethoxypropanoic acid.

Example 1

Preparation of
2-(2,4-dimethyl-1,3-dioxolan-2-yl)acetic acid
[compound (IIa)]

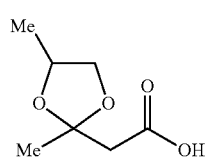

The acid 2-(2,4-dimethyl-1,3-dioxolan-2-yl)acetic acid was obtained as a derivative from saponification of the ester ethyl 2-(2,4-dimethyl-1,3-dioxolan-2-yl)acetate. The hydrolysis of ethyl 2-(2,4-dimethyl-1,3-dioxolan-2-yl)acetate in alkaline medium is described in different publications: a) Miranda et al., *Tetrahedron*, 1987, 143; b) Lelandais et al., *Can. J. Chem.*, 1983, 584; c) Oku et al., *J. Org. Chem.*, 1997, 2123. The acid was obtained with variable yields 50-82%.

3.6 g of ethyl 2-(2,4-dimethyl-1,3-dioxolan-2-yl)acetate in a solution of 1.18 g (1.1 equiv.) of KOH in 8 mL of water were mixed at room temperature under magnetic stirring. After 4 h, the basic aqueous layer was removed with 5 mL of tert-butyl methyl ether, recovering 257 mg (7%) from the starting material. The aqueous layer was brought to dryness. The residue was stirred in a mixture with 2 ml NaCl-saturated water and 8 mL of $CH_2Cl_2$ under vigorous stirring. $H_2SO_4$ were added until achieving an acidic pH. The organic layers were dried with sodium sulphate, filtered off and evaporated obtaining 2.344 g of the title compound (82% considering the previously recovered 7%).

Example 2

Preparation of 3,3-diethoxypropanoic acid

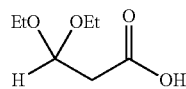

Ref. F. Zaragoza et al, J. Med. Chem., 2005, 48(1), 306.

To a 250 mL round-bottomed flask with magnetic stirring that contained ethyl 3,3-diethoxypropanoate (20.0 g, 102.0 mmol, colourless oil, 97%), a previously prepared solution of NaOH (5.23 g, 131.0 mmol) in $H_2O$ (30 mL) was added. The resulting mixture was stirred to reflux (100° C.) during 1 h. After allowing it to temper, the mixture was acidified using HCl 37% and it was extracted with AcOEt, 8×20 mL. The resulting organic phase was washed with 1×20 mL NaCl sat., dried with $Na_2SO_4$, filtered and concentrated to dryness. The obtained oil was confirmed to correspond to the title compound (15.9 g, 98.0 mmol, 96%).

Synthesis of the compound of formula (V) 2-(2,4-dimethyl-1,3-dioxolan-2-yl)-N'-(naphthalen-2-yl)acetohydrazide via step a1)

Example 3

Preparation of the Compound of Formula (V) 2-(2,4-dimethyl-1,3-dioxolan-2-yl)-1V-(naphthalen-2-yl)acetohydrazide using EDC

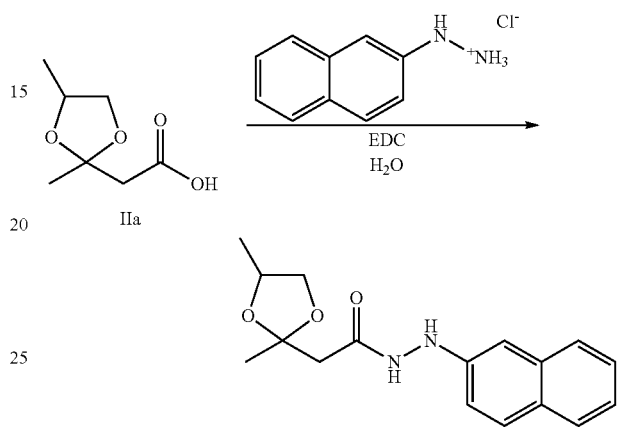

A solution of EDC (1.307 g, 6.82 mmol) in 10 mL of water was added to a suspension of the compound of formula (IV) naphthalen-2-ylhydrazyne hydrochloride (1.236 g, 6.35 mmol) and the compound (IIa) 2-(2,4-dimethyl-1,3-dioxolan-2-yl)acetic acid (1.072 g, 6.69 mmol) in 30 mL of water. After 15 minutes the reaction mixture was filtered and the solution was washed with 40 mL of $10^{-3}$M HCl and then 40 mL of water. The organic layer was dried over $MgSO_4$ and after filtering the solvent was evaporated to dryness. The corresponding 0.705 g (37%) of the title hydrazide was obtained. Further cyclation was not carried out.

Synthesis of the Compound of Formula (VII)/(VIIa) 5-methyl-1-(naphthalen-2-yl)-1H-pyrazol-3-ol via step a1)

The following reaction scheme shows the chemical transformations taking place in examples 4-21.

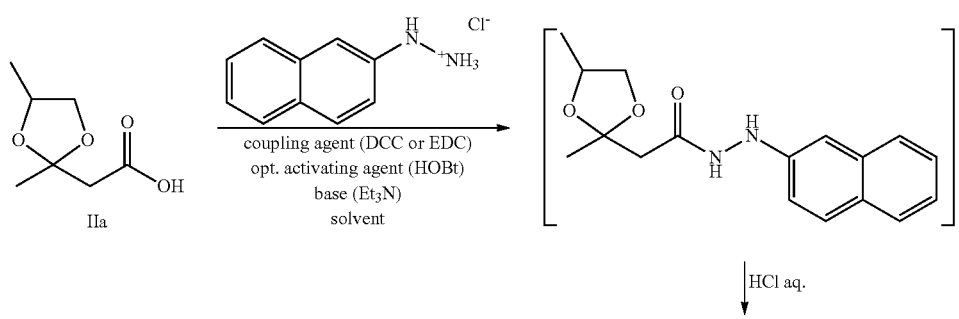

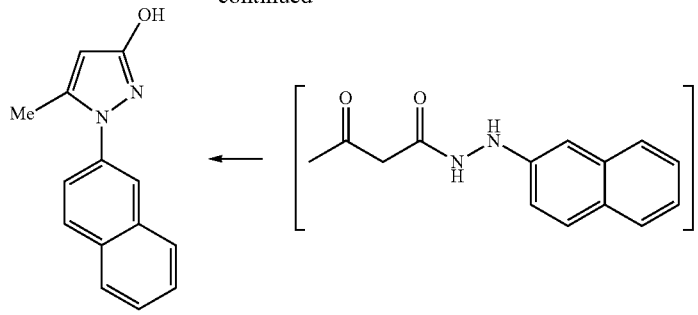

Example 4

Preparation of the Compound of Formula (VII)/(VIIa) 5-methyl-1-(naphthalen-2-yl)-1H-pyrazol-3-ol with DCC A solution of dicyclohexylcarbodiimide (DCC, 1.629 g, 7.91 mmol, 1.07 equiv.) in 14 mL of anhydrous methylene chloride was added to a suspension of the compound of formula (IV) naphthalen-2-ylhydrazyne hydrochloride (1.434 g, 7.37 mmol), the compound (IIa) 2-(2,4-dimethyl-1,3-dioxolan-2-yl)acetic acid (1.242 g, 7.75 mmol, 1.05 equiv.), and triethylamine (1070 µL, 7.75 mmol, 1.05 equiv.) in 10 mL of anhydrous methylene chloride. After 20 minutes the reaction was considered to be completed. The solid was filtered and the crude was then washed with 40 mL of $10^{-3}$M HCl and then with 40 mL of water. The organic layer was dried over $MgSO_4$ and after filtering the solvent, it was evaporated to dryness, to obtain the compound of formula (V) 2-(2,4-dimethyl-1,3-dioxolan-2-yl)-N'-(naphthalen-2-yl)acetohydrazide.

The dry crude was dissolved in 100 mL of MeOH. A solution of HCl in water (2 mL of concentrated HCl in 5 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 1.334 g (81%) of a solid was obtained corresponding to the title compound. The isomeric ratio obtained for [5-methyl-1-(naphthalen-2-yl)-1H-pyrazol-3-ol]:[3-methyl-1-(naphthalen-2-yl)-1H-pyrazol-5-ol] was 98:2.

Example 5

Preparation of the Compound of Formula (VII)/(VIIa) 5-methyl-1-(naphthalen-2-yl)-1H-pyrazol-3-ol using DCC A solution of DCC (1.644 g, 7.95 mmol) in 8 mL of MeOH was added to a suspension of the compound of formula (IV) naphthalen-2-ylhydrazyne hydrochloride (1.406 g, 7.22 mmol), the compound (IIa) 2-(2,4-dimethyl-1,3-dioxolan-2-yl)acetic acid (1.273 g, 7.95 mmol), and triethylamine (1050 µL, 7.59 mmol) in 6 mL of MeOH. After 20 minutes the reaction was considered to be completed. It was filtered and brought to dryness to obtain the compound of formula (V) 2-(2,4-dimethyl-1,3-dioxolan-2-yl)-N'-(naphthalen-2-yl)acetohydrazide.

The dry crude was dissolved in 100 mL of MeOH. A solution of HCl in water (2 mL of concentrated HCl in 5 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 0.894 g (55%) of a solid was obtained corresponding to the title compound. The isomeric ratio obtained for [5-methyl-1-(naphthalen-2-yl)-1H-pyrazol-3-ol]:[3-methyl-1-(naphthalen-2-yl)-1H-pyrazol-5-ol] was 99.5:0.5.

Example 6

Preparation of the Compound of Formula (VII)/(VIIa) 5-methyl-1-(naphthalen-2-yl)-1H-pyrazol-3-ol using DCC A solution of DCC (8.098 g, 39.25 mmol, 1.1 equiv.) in 15 mL of anhydrous methylene chloride was added to a suspension of the compound of formula (IV) naphthalen-2-ylhydrazyne hydrochloride (6.944 g, 35.67 mmol), the compound (IIa) 2-(2,4-dimethyl-1,3-dioxolan-2-yl)acetic acid (6.282 g, 39.22 mmol, 1.1 equiv.), and triethylamine (5.2 mL, 37.46 mmol, 1.05 equiv.) in 35 mL of anhydrous methylene chloride. After 20 minutes the reaction was considered to be completed. The solid was filtered and the crude was then washed with 80 mL of $10^{-3}$M HCl and then with 80 mL of water. The organic layer was dried over $MgSO_4$ and after filtering the solvent, it was evaporated to dryness to obtain the compound of formula (V) 2-(2,4-dimethyl-1,3-dioxolan-2-yl)-N'-(naphthalen-2-yl)acetohydrazide.

The dry crude was dissolved in 200 mL of MeOH. A solution of HCl in water (4 mL of concentrated HCl in 10 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH (≈40 mL) obtaining a precipitate.

The basified crude was filtered and the filtrate thus obtained was acidified with dilute AcOH (1:5 with water) to pH≈7. During the neutralisation a new precipitate was observed, which was then filtered and dried in a desiccator. 5.488 g (69%) of a solid was obtained corresponding to the title compound.

Example 7

Preparation of the Compound of Formula (VII)/ (VIIa) 5-methyl-1-(naphthalen-2-yl)-1H-pyrazol-3-ol using DCC A solution of DCC (8.122 g, 39.36 mmol, 1.1 equiv.) in 20 mL of methylene chloride was added at 0° C. to a suspension of the compound of formula (IV) naphthalen-2-ylhydrazyne hydrochloride (6.942 g, 35.67 mmol), the compound (IIa) 2-(2,4-dimethyl-1,3-dioxolan-2-yl)acetic acid (6.575 g, 41.05 mmol, 1.15 equiv.), and triethylamine (5.4 mL, 39.24 mmol, 1.1 equiv.) in 40 mL of methylene chloride. After 60 minutes the reaction was considered to be completed. The solid was filtered and the crude was then washed with 80 mL of $10^{-3}$M HCl and then with 80 mL of water. The organic layer was dried over $MgSO_4$ and after filtering the solvent, it was evaporated to dryness to obtain the compound of formula (V) 2-(2,4-dimethyl-1,3-dioxolan-2-yl)-N'-(naphthalen-2-yl)acetohydrazide.

The dry crude was dissolved in 200 mL of MeOH. A solution of HCl in water (4 mL of concentrated HCl in 10 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 4M NaOH (≈20 mL) obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 8.9 g (>100%) of a solid was obtained corresponding to the title compound.

Washes: A suspension of the solid crude (8.9 g) was heated to reflux for 1 h in 50 mL of MeOH. It was cold filtered. The solid was washed with 20 mL of cold MeOH yielding 5.321 g (56%) of the title compound.

Example 8

Preparation of the Compound of Formula (VII)/ (VIIa) 5-methyl-1-(naphthalen-2-yl)-1H-pyrazol-3-ol using DCC A mixture of DCC (5.906 g, 28.62 mmol, 1.1 equiv.) and the compound (IIa) 2-(2,4-dimethyl-1,3-dioxolan-2-yl)acetic acid (4.317 g, 26.97 mmol, 1.05 equiv.) in 25 mL of methylene chloride was slowly added at 0° C. to a suspension of the compound of formula (IV) naphthalen-2-ylhydrazyne hydrochloride (4.999 g, 25.69 mmol), and triethylamine (3.7 mL, 26.97 mmol, 1.05 equiv.) in 50 mL of methylene chloride. After 60 minutes the solid was filtered and the crude was then washed with 80 mL of $10^{-3}$M HCl and then with 80 mL of water. The organic layer was dried over $MgSO_4$ and after filtering the solvent was evaporated to dryness to obtain the compound of formula (V) 2-(2,4-dimethyl-1,3-dioxolan-2-yl)-N'-(naphthalen-2-yl)acetohydrazide.

The dry crude was dissolved in 130 mL of MeOH. A solution of HCl in water (3 mL of concentrated HCl in 7 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH (≈40 mL) obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 3.223 g (56%) of a solid was obtained corresponding to the title compound.

Washes: A suspension of the solid crude (3.101 g) was heated to reflux for 1 h in 30 mL of MeOH. It was cold filtered. The solid was washed with 10 mL of cold MeOH yielding 2.183 g (38%) of the title compound.

Example 9

Preparation of the Compound of Formula (VII)/ (VIIa) 5-methyl-1-(naphthalen-2-yl)-1H-pyrazol-3-ol using DCC A solution of DCC (5.861 g, 28.41 mmol, 1.1 equiv.) in 20 mL of toluene was added to a dense suspension of the compound of formula (IV) naphthalen-2-ylhydrazyne hydrochloride (4.993 g, 25.69 mmol), the compound (IIa) 2-(2,4-dimethyl-1,3-dioxolan-2-yl)acetic acid (4.588 g, 28.64 mmol, 1.10 equiv.), and triethylamine (3.7 mL, 26.97 mmol, 1.05 equiv.) in 25 mL of toluene. After 60 minutes the solid was filtered and the crude was then washed with 80 mL of $10^{-3}$M HCl and then with 80 mL of water. The organic layer was dried over $MgSO_4$ and after filtering the solvent, it was evaporated to dryness to obtain the compound of formula (V) 2-(2, 4-dimethyl-1,3-dioxolan-2-yl)-N'-(naphthalen-2-yl)acetohydrazide.

The dry crude was dissolved in 130 mL of MeOH. A solution of HCl in water (3 mL of concentrated HCl in 7 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH (≈40 mL) obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 5.032 g (87%) of a solid was obtained corresponding to the title compound.

Example 10

Preparation of the Compound of Formula (VII)/ (VIIa) 5-methyl-1-(naphthalen-2-yl)-1H-pyrazol-3-ol using DCC A solution of DCC (5.844 g, 28.32 mmol, 1.1 equiv.) in 20 mL of THF was added at 0° C. to a suspension of the compound of formula (IV) naphthalen-2-ylhydrazyne hydrochloride (5.004 g, 25.71 mmol), the compound (IIa) 2-(2,4-dimethyl-1,3-dioxolan-2-yl)acetic acid (4.330 g, 27.03 mmol, 1.05 equiv.), and triethylamine (3.7 mL, 26.97 mmol, 1.05 equiv.) in 40 mL of THF. After 100 minutes the solid was filtered and the solvent was evaporated to dryness to obtain the compound of formula (V) 2-(2,4-dimethyl-1,3-dioxolan-2-yl)-N'-(naphthalen-2-yl)acetohydrazide.

The dry crude was dissolved in 130 mL of MeOH. A solution of HCl in water (3 mL of concentrated HCl in 7 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH (≈40 mL) obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 4.729 g (82%) of a solid was obtained corresponding to the title compound.

Washes: A suspension of the solid crude (4.589 g) was heated reflux for 30 min in 10 mL of ethyl acetate. It was cold filtered. The solid was washed with 6 mL of cold ethyl acetate yielding 3.041 g (53%) of the title compound.

Example 11

Preparation of the Compound of Formula (VII)/ (VIIa) 5-methyl-1-(naphthalen-2-yl)-1H-pyrazol-3-ol using DCC A solution of DCC (5.823 g, 28.22 mmol, 1.1 equiv.) in 20 mL of AcOEt was added to a suspension of the compound of formula (IV) naphthalen-2-ylhydrazyne hydrochloride (4.988 g, 25.62 mmol), the compound (IIa) 2-(2,4-dimethyl-1,3-dioxolan-2-yl)acetic acid (4.352 g, 27.17 mmol, 1.05 equiv.), and triethylamine (3.7 mL, 26.97 mmol, 1.05 equiv.) in 40 mL of AcOEt. After 60 minutes solid was filtered and the crude was then washed with 60 mL of $10^{-3}$M HCl and then with 60 mL of water. The organic layer was dried over $MgSO_4$ and after filtering the solvent was evaporated to dryness to obtain the compound of formula (V) 2-(2,4-dimethyl-1,3-dioxolan-2-yl)-N'-(naphthalen-2-yl)acetohydrazide.

The dry crude was dissolved in 130 mL of MeOH. A solution of HCl in water (3 mL of concentrated HCl in 7 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH (≈40 mL) obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 3.614 g (62%) of a solid was obtained corresponding to the title compound.

Example 12

Preparation of the Compound of Formula (VII)/ (VIIa) 5-methyl-1-(naphthalen-2-yl)-1H-pyrazol-3-ol using DCC A solution of DCC (5.842 g, 28.31 mmol, 1.1 equiv.) in 20 mL of $CH_3CN$ was added at 0° C. to a suspension of the compound of formula (IV) naphthalen-2-ylhydrazyne hydrochloride (4.994 g, 25.65 mmol), the compound (IIa) 2-(2,4-dimethyl-1,3-dioxolan-2-yl)acetic acid (4.354 g, 26.97 mmol, 1.05 equiv.), and triethylamine (3.7 mL, 26.97 mmol, 1.05 equiv.) in 40 mL of $CH_3CN$. After 60 minutes the solid was filtered and the solvent was evaporated to dryness to obtain the compound of formula (V) 2-(2,4-dimethyl-1,3-dioxolan-2-yl)-N'-(naphthalen-2-yl)acetohydrazide.

The dry crude was dissolved in 130 mL of MeOH. A solution of HCl in water (3 mL of concentrated HCl in 7 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH (≈40 mL) obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 3.791 g (66%) of a solid was obtained corresponding to the title compound.

Example 13

Preparation of the Compound of Formula (VII)/ (VIIa) 5-methyl-1-(naphthalen-2-yl)-1H-pyrazol-3-ol using DCC A solution of DCC (5.542 g, 26.86 mmol, 1.1 equiv.) in 20 mL of isopropanol was added at 0° C. to a suspension of the compound of formula (IV) naphthalen-2-ylhydrazyne hydrochloride (4.720 g, 24.25 mmol), the compound (IIa) 2-(2,4-dimethyl-1,3-dioxolan-2-yl)acetic acid (4.095 g, 25.57 mmol, 1.05 equiv.), and triethylamine (3.5 mL, 25.46 mmol, 1.05 equiv.) in 40 mL of $CH_3CN$. After 60 minutes the solid was filtered and the solvent was evaporated to dryness to obtain the compound of formula (V) 2-(2,4-dimethyl-1,3-dioxolan-2-yl)-N-(naphthalen-2-yl)acetohydrazide.

The dry crude was dissolved in 130 mL of MeOH. A solution of HCl in water (3 mL of concentrated HCl in 7 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH (≈40 mL) obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 2.587 g (48%) of a solid was obtained corresponding to the title compound.

Example 14

Preparation of the Compound of Formula (VII)/ (VIIa) 5-methyl-1-(naphthalen-2-yl)-1H-pyrazol-3-ol using DCC Over a solution of the compound (IIa) 2-(2,4-dimethyl-1,3-dioxolan-2-yl)acetic acid (8.68 kg, 54.2 mol) in methylene chloride (35 L), triethylamine (5.7 kg, 56.6 mol), the compound of formula (IV) naphthalen-2-ylhydrazyne hydrochloride (10.5 kg, 53.9 mol) and a solution of dicyclohexylcarbodiimide (11.3 kg, 55.0 mol) in methylene chloride (13 L) were added. It was refluxed until the proper reaction control, was cooled at room temperature and the suspension solid was filtered, washed with methylene chloride (10.5 L). Methylene chloride was distilled and the obtained compound of formula (V) 2-(2,4-dimethyl-1,3-dioxolan-2-yl)-N'-(naphthalen-2-yl)acetohydrazide was dissolved in methanol (157 L) and 35% HCl (6.3 L) and water (19 L) were added. The mixture was refluxed for 1 hour to hydrolize the ketal group, thus obtaining the compound of formula (VI) N'-(naphthalen-2-yl)-3-oxobutanehydrazide which subsequently cyclises. Methanol was distilled, water was added (42 L) and the solution was washed with methylene chloride at basic pH. The organic layer was removed and pH of aqueous layer fitted to 6. The precipitated solid was centrifuged, washed with water (15 L) and suspended on ethyl acetate (37 L). It was centrifuged, washed with ethyl acetate (5 L) and vacuum dried at 50° C. 8.7 kg of 5-methyl-1-(naphthalen-2-yl)-1H-pyrazol-3-ol (yield 72%) was obtained. No isomer was detected.

Example 15

Preparation of the Compound of Formula (VII)/ (VIIa) 5-methyl-1-(naphthalen-2-yl)-1H-pyrazol-3-ol using DCC and HOBt A solution of DCC (5.853 g, 28.37 mmol, 1.1 equiv.) in 20 mL of toluene was added at 0° C. to a suspension of the compound of formula (IV) naphthalen-2-ylhydrazyne hydrochloride (4.999 g, 25.69 mmol), the compound (IIa) 2-(2,4-dimethyl-1,3-dioxolan-2-yl)acetic acid (4.351 g, 27.16 mmol, 1.05 equiv.), triethylamine (3.7 mL, 26.97 mmol, 1.05 equiv.), and 1-hydroxybenzotriazole hydrate (HOBt) (201 mg, 1.31 mmol) in 40 mL of toluene. The reaction was kept at 0° C. for one hour. After 60 minutes the solid was filtered and the crude was then washed with 60 mL of $10^{-3}$M HCl and 60 mL of water. The organic layer was dried over $MgSO_4$ and finally the solvent was evaporated to dryness to obtain the compound of formula (V) 2-(2,4-dimethyl-1,3-dioxolan-2-yl)-N'-(naphthalen-2-yl)acetohydrazide.

The dry crude was dissolved in 130 mL of MeOH. A solution of HCl in water (3 mL of concentrated HCl in 7 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH (≈40 mL) obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 4.086 g (71%) of a solid was obtained corresponding to the title compound. The isomeric ratio obtained for [5-methyl-1-(naphthalen-2-yl)-1H-pyrazol-3-ol]:[3-methyl-1-(naphthalen-2-yl)-1H-pyrazol-5-ol] was 99.5:0.5.

Example 16

Preparation of the Compound of Formula (VII)/ (VIIa) 5-methyl-1-(naphthalen-2-yl)-1H-pyrazol-3-ol using DCC and HOBt A solution of DCC (5.830 g, 28.26 mmol, 1.1 equiv.) in 20 mL of toluene was added at 0° C. to a suspension of the compound of formula (IV) naphthalen-2-ylhydrazyne hydrochloride (5.012 g, 25.75 mmol), the compound (IIa) 2-(2,4-dimethyl-1,3-dioxolan-2-yl)acetic acid (4.329 g, 27.03 mmol, 1.05 equiv.), triethylamine (3.7 mL, 26.97 mmol, 1.05 equiv.), and HOBt (201 mg, 1.31 mmol) in 40 mL of toluene. The reaction was kept at 0° C. for two hours. After 60 minutes the solid was filtered and the filtrate was evaporated to dryness to obtain the compound of formula (V) 2-(2,4-dimethyl-1,3-dioxolan-2-yl)-N-(naphthalen-2-yl)acetohydrazide.

The dry crude was dissolved in 130 mL of MeOH. A solution of HCl in water (3 mL of concentrated HCl in 7 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH (≈40 mL) obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 4.495 (78%) of a solid was obtained corresponding to the title compound. The isomeric ratio obtained for [5-methyl-1-(naphthalen-2-yl)-1H-pyrazol-3-ol]:[3-methyl-1-(naphthalen-2-yl)-1H-pyrazol-5-ol] was 99.5:0.5.

Example 17

Preparation of the Compound of Formula (VII)/ (VIIa) 5-methyl-1-(naphthalen-2-yl)-1H-pyrazol-3-ol using DCC and HOBt A solution of DCC (17.526 g, 84.94 mmol, 1.1 equiv.) in 60 mL of toluene was added at 0° C. to a suspension of the compound of formula (IV) naphthalen-2-ylhydrazyne hydrochloride (14.991 g, 77.01 mmol), the compound (IIa) 2-(2,4-dimethyl-1,3-dioxolan-2-yl)acetic acid (13.016 g, 81.26 mmol, 1.05 equiv.), triethylamine (11.2 mL, 80.91 mmol, 1.05 equiv.), and HOBt (593 mg, 3.87 mmol) in 120 mL of toluene. The reaction was kept at 0° C. for one hour and 15 minutes. After 60 minutes the solid was filtered and the crude was then washed with 180 mL of $10^{-3}$M HCl and 180 mL of water. Finally the solvent from the organic layer was evaporated to dryness to obtain the compound of formula (V) 2-(2,4-dimethyl-1,3-dioxolan-2-yl)-N'-(naphthalen-2-yl) acetohydrazide.

The dry crude was dissolved in 250 mL of MeOH. A solution of HCl in water (9 mL of concentrated HCl in 21 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH (≈40 mL) obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 14.020 g (81%) of a solid was obtained corresponding to the title compound. The isomeric ratio obtained for [5-methyl-1-(naphthalen-2-yl)-1H-pyrazol-3-ol]:[3-methyl-1-(naphthalen-2-yl)-1H-pyrazol-5-ol] was 99.5:0.5.

Example 18

Preparation of the Compound of Formula (VII)/(VIIa) 5-methyl-1-(naphthalen-2-yl)-1H-pyrazol-3-ol using DCC and HOBt A solution of DCC (5.859 g, 28.40 mmol, 1.1 equiv.) in 20 mL of $CH_2Cl_2$ was added at 0° C. to a suspension of the compound of formula (IV) naphthalen-2-ylhydrazyne hydrochloride (5.007 g, 25.72 mmol), the compound (IIa) 2-(2,4-dimethyl-1,3-dioxolan-2-yl)acetic acid (4.331 g, 27.04 mmol, 1.05 equiv.), triethylamine (3.7 mL, 26.97 mmol, 1.05 equiv.), and HOBt (199 mg, 1.30 mmol) in 40 mL of $CH_2Cl_2$. The reaction was kept at 0° C. for one hour. After 60 minutes the solid was filtered, the filtrate was then washed with 60 mL of $10^{-3}$M HCl and 60 mL of water and the organic layer was dried over $MgSO_4$. Finally the solvent was evaporated to dryness to obtain the compound of formula (V) 2-(2,4-dimethyl-1,3-dioxolan-2-yl)-N'-(naphthalen-2-yl)acetohydrazide.

The dry crude was dissolved in 130 mL of MeOH. A solution of HCl in water (3 mL of concentrated HCl in 7 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH (≈40 mL) obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 5.136 g (89%) of a solid was obtained corresponding to the title compound. The isomeric ratio obtained for [5-methyl-1-(naphthalen-2-yl)-1H-pyrazol-3-ol]:[3-methyl-1-(naphthalen-2-yl)-1H-pyrazol-5-ol] was 99.5:0.5.

Example 19

Preparation of the Compound of Formula (VII)/(VIIa) 5-methyl-1-(naphthalen-2-yl)-1H-pyrazol-3-ol using DCC and HOBt A solution of DCC (5.830 g, 28.26 mmol, 1.1 equiv.) in 20 mL of MeOH was added at 0° C. to a suspension of the compound of formula (IV) naphthalen-2-ylhydrazyne hydrochloride (5.006 g, 25.72 mmol), the compound (IL) 2-(2,4-dimethyl-1,3-dioxolan-2-yl)acetic acid (4.337 g, 27.08 mmol, 1.05 equiv.), triethylamine (3.7 mL, 26.97 mmol, 1.05 equiv.), and HOBt (197 mg, 1.28 mmol) in 40 mL of MeOH. The reaction was kept at 0° C. for one hour. After 60 minutes the solid was filtered and the solvent was evaporated to dryness to obtain the compound of formula (V) 2-(2,4-dimethyl-1,3-dioxolan-2-yl)-N'-(naphthalen-2-yl)acetohydrazide.

The dry crude was dissolved in 130 mL of MeOH. A solution of HCl in water (3 mL of concentrated HCl in 7 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH (≈40 mL) obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 2.248 g (39%) of a solid was obtained corresponding to the title compound. The isomeric ratio obtained for [5-methyl-1-(naphthalen-2-yl)-1H-pyrazol-3-ol]:[3-methyl-1-(naphthalen-2-yl)-1H-pyrazol-5-ol] was 99.5:0.5.

Example 20

Preparation of the Compound of Formula (VII)/(VIIa) 5-methyl-1-(naphthalen-2-yl)-1H-pyrazol-3-ol using EDC A solution of N-(3-dimethylaminopropyl)-N'-ethylcarbodiimide (EDC, 1.439 g, 7.51 mmol) in 14 mL of anhydrous methylene chloride was added to a suspension of the compound of formula (IV) naphthalen-2-ylhydrazyne hydrochloride (1.357 g, 6.99 mmol), the compound (IIa) 2-(2,4-dimethyl-1,3-dioxolan-2-yl)acetic acid (1.179 g, 7.36 mmol), and triethylamine (1020 µL, 7.36 mmol) in 6 mL of anhydrous methylene chloride. After 15 minutes the solution was washed with 40 mL of $10^{-3}$M HCl and then 40 mL of water. The organic layer was dried over $MgSO_4$ and after filtering the solvent, it was evaporated to dryness to obtain the compound of formula (V) 2-(2,4-dimethyl-1,3-dioxolan-2-yl)-N'-(naphthalen-2-yl)acetohydrazide.

The dry crude was dissolved in 100 mL of MeOH. A solution of HCl in water (2 mL of concentrated HCl in 5 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume (to ≈10-15 ml). This evaporated crude was basified to pH≈14 with 2M NaOH (≈40 mL) obtaining a precipitate. The basified crude was filtered, the solid was discarded and the filtrate thus obtained was acidified with dilute AcOH (1:5 with water) to pH≈7. During the neutralisation a new precipitate was observed, which was then filtered and dried in a desiccator. 1.301 g (83%) of a solid was obtained corresponding to the title compound. The isomeric ratio obtained for [5-methyl-1-(naphthalen-2-yl)-1H-pyrazol-3-ol]:[3-methyl-1-(naphthalen-2-yl)-1H-pyrazol-5-ol] was 99.5:0.5.

Example 21

Preparation of the Compound of Formula (VII)/
(VIIa) 5-methyl-1-(naphthalen-2-yl)-1H-pyrazol-3-ol
using EDC A solution of EDC (5.041 g, 26.30 mmol, 1.16 equiv.) in 15 mL of methylene chloride was added to a suspension at 0° C. of the compound of formula (IV) naphthalen-2-ylhydrazyne hydrochloride (4.414 g, 22.68 mmol, 1 equiv.), the compound (IIa) 2-(2,4-dimethyl-1,3-dioxolan-2-yl)acetic acid (4.030 g, 25.16 mmol, 1.1 equiv.), and triethylamine (3.5 mL, 24.95 mmol, 1.1 equiv.) in 35 mL of anhydrous methylene chloride.

After 15 minutes the reaction mixture was washed with 80 mL of $10^{-3}$M HCl and then 80 mL of water. The organic layer was dried over $MgSO_4$ and after filtering the solvent, it was evaporated to dryness to obtain the compound of formula (V) 2-(2,4-dimethyl-1,3-dioxolan-2-yl)-N'-(naphthalen-2-yl)-acetohydrazide.

The dry crude was dissolved in 130 mL of MeOH. A solution of HCl in water (3 mL of concentrated HCl in 7 mL of water) was added and the reaction was refluxed for one hour to hydrolize the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume (to ≈10-15 ml). This evaporated crude was basified to pH≈14 with 4M NaOH obtaining a precipitate. The basified crude was filtered, the solid was discarded and the filtrate thus obtained was acidified with dilute AcOH (1:5 with water) to pH≈7. During the neutralisation a new precipitate was observed, which was then filtered and dried in a desiccator. 4.613 g (91%) of a solid was obtained corresponding to the title compound. The isomeric ratio obtained for [5-methyl-1-(naphthalen-2-yl)-1H-pyrazol-3-ol]:[3-methyl-1-(naphthalen-2-yl)-1H-pyrazol-5-ol] was 99.5:0.5.

Synthesis of the compound of formula (VII)/(VIIa)
5-methyl-1-(naphthalen-2-yl)-1H-pyrazol-3-ol via
step a2)

The following reaction scheme shows the chemical transformations taking place in examples 22-23.

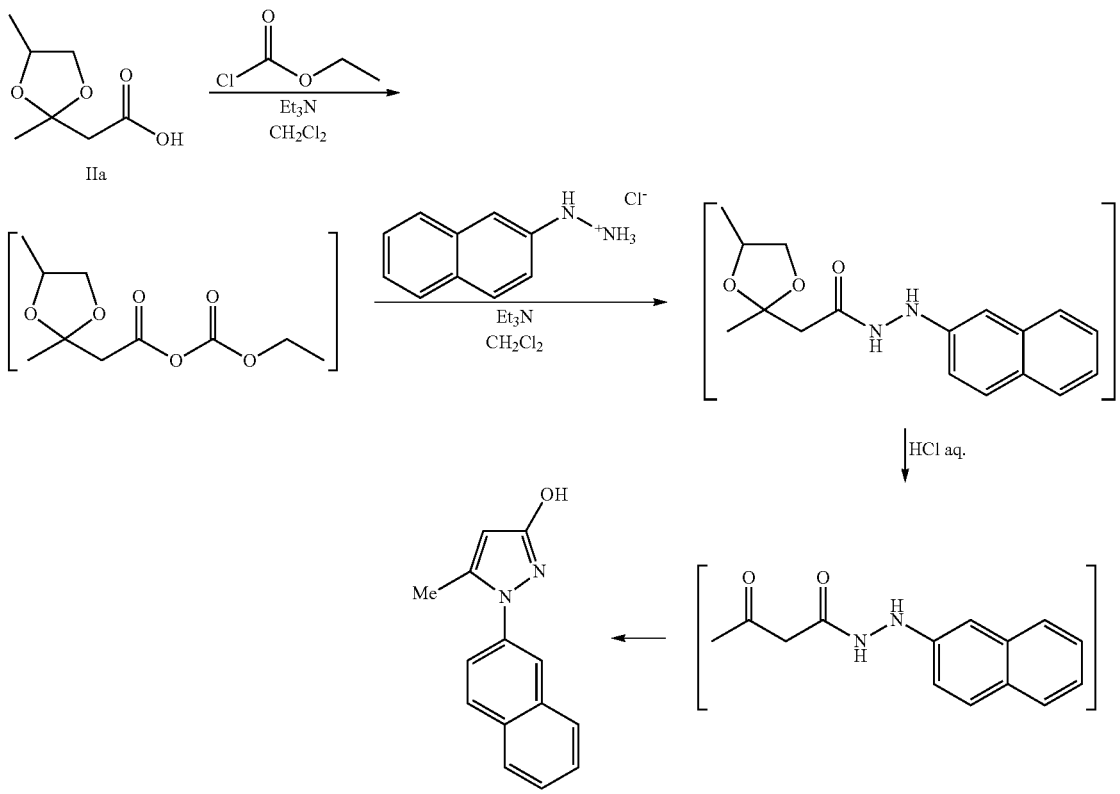

Example 22

Preparation of the Compound of Formula (VII)/
(VIIa) 5-methyl-1-(naphthalen-2-yl)-1H-pyrazol-3-ol
via mixed anhydrides of formula (III)

Over a solution of the compound (IIa) 2-(2,4-dimethyl-1, 3-dioxolan-2-yl)acetic acid (4.320 g, 26.97 mmol) in 50 mL of $CH_2Cl_2$, ethyl chloroformate (2.5 mL, 25.75 mmol) at 0° C. was added. Keeping temperature at 0° C. anhydrous $Et_3N$ (3.9 mL, 28.26 mmol) was slowly added to obtain the compound of formula (III) ethyl carbonic 2-(2,4-dimethyl-1,3-dioxolan-2-yl)acetic anhydride. After 20 minutes of stirring, a suspension of the compound of formula (IV) naphthalen-2-ylhydrazyne hydrochloride (5.007 g, 25.69 mmol) and $Et_3N$ (3.9 mL, 28.26 mmol) in 35 mL of anhydrous $CH_2Cl_2$ was added at r.t. over the mixed anhydride. After 3 hours solvent was evaporated to obtain the compound of formula (V) 2-(2, 4-dimethyl-1,3-dioxolan-2-yl)-N'-(naphthalen-2-yl) acetohydrazide.

The dry crude was dissolved in 130 mL of MeOH. A solution of HCl in water (3 mL of concentrated HCl in 7 mL of water) was added and the reaction was refluxed for one hour to hydrolyze the ketal group, thus obtaining the compound of formula (VI) N'-(naphthalen-2-yl)-3-oxobutanehydrazide which subsequently cyclises. The reaction was allowed to cool to room temperature. The crude was then concentrated in a rotavapor so as to reduce as much as possible the MeOH volume. This evaporated crude was basified to pH≈14 with 2M NaOH (≈40 mL) obtaining a precipitate. The basified crude was filtered, the solid was discarded and the filtrate thus obtained was acidified with dilute AcOH (1:5 with water) to pH≈7. During the neutralisation a new precipitate was observed, which was then filtered and dried in a desiccator. 5.612 g (97%) of a solid was obtained corresponding to the title compound according to $^1$H NMR. The isomeric ratio obtained for [5-methyl-1-(naphthalen-2-yl)-1H-pyrazol-3-ol]:[3-methyl-1-(naphthalen-2-yl)-1H-pyrazol-5-ol] was 98:2.

Example 23

Preparation of the Compound of Formula (VII)/ (VIIa) 5-methyl-1-(naphthalen-2-yl)-1H-pyrazol-3-ol via mixed anhydrides of formula (III)

Over a solution of the compound (IIa) 2-(2,4-dimethyl-1,3-dioxolan-2-yl)acetic acid (3.06 kg, 19.1 mol) in methylene chloride (27.5 L), triethylamine (4.1 kg, 40.1 mol) and ethyl chloroformate (2.0 kg, 18.7 mol) were added at 0/5° C. to obtain the compound of formula (III) ethyl carbonic 2-(2,4-dimethyl-1,3-dioxolan-2-yl)acetic anhydride. The compound of formula (IV) naphthalen-2-ylhydrazyne hydrochloride (3.69 kg, 20.0 mol) was added and stirred at room temperature until the proper reaction control. Methylene chloride was distilled and the obtained compound of formula (V) 2-(2,4-dimethyl-1,3-dioxolan-2-yl)-N'-(naphthalen-2-yl)acetohydrazide was dissolved in methanol (44 L) and 35% HCl (2.2 L) and water (6.5 L) were added. The mixture was refluxed for 1 hour to hydrolize the ketal group, thus obtaining the compound of formula (VI) N'-(naphthalen-2-yl)-3-oxobutanehydrazide which subsequently cyclises. Methanol was distilled, water was added (15 L) and the solution was washed with methylene chloride at basic pH. The organic layer was removed and pH of aqueous layer fitted to 6. The precipitated solid was centrifuged, washed with water (7.5 L) and vacuum dried at 50° C. 3.7 kg of 5-methyl-1-(naphthalen-2-yl)-1H-pyrazol-3-ol (yield 86%) was obtained.

The following reaction scheme shows the chemical transformations taking place in examples 24-25.

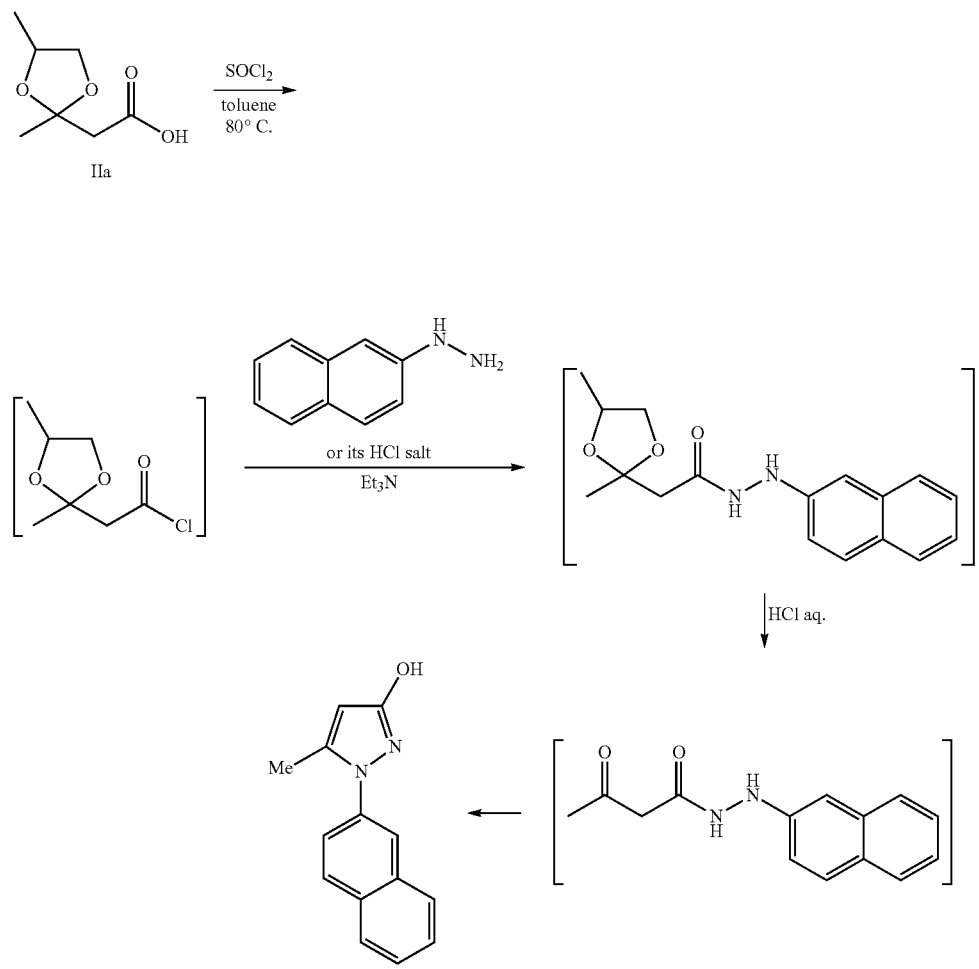

Example 24

Preparation of the Compound of Formula (VII)/ (VIIa) 5-methyl-1-(naphthalen-2-yl)-1H-pyrazol-3-ol using via acid chloride of formula (III)

An amount of the compound (IIa) 2-(2,4-dimethyl-1,3-dioxolan-2-yl)acetic acid (1.043 g, 6.51 mmol) was dissolved in 20 ml of toluene. Under stirring, thionyl chloride (550 μL, 7.49 mmol, 1.15 equiv.) was added and the solution was heated at 80° C. for 2 h 15 min After this period of time, the solution was allowed to cool to room temperature and reduced by half the volume of toluene by distillation, thus obtaining a solution of the compound of formula (III) 2-(2,4-dimethyl-1,3-dioxolan-2-yl)acetyl chloride.

This solution of acid chloride in toluene was cannulated over a solution of the compound of formula (IV) naphthalen-2-ylhydrazyne (free base, 1.072 g, 6.84 mmol) and $Et_3N$ (1350 μL, 9.76 mmol) in 10 mL of methylene chloride in an ice bath. Once acid chloride was added the cool bath was removed and the mixture was stirred at rt for 45 minutes. After this period of time, the reaction mixture was concentrated to dryness to obtain the compound of formula (V) 2-(2,4-dimethyl-1,3-dioxolan-2-yl)-N'-(naphthalen-2-yl)acetohydrazide.

The dry crude was dissolved in 100 mL of MeOH. A solution of HCl in water (2 mL of concentrated HCl in 5 mL of water) was added to hydrolize the ketal group, thus obtaining the compound of formula (VI) N'-(naphthalen-2-yl)-3-oxobutanehydrazide which subsequently cyclises. The reaction was refluxed for one hour and was allowed to cool to room temperature. The crude was then concentrated in a rotavapor so as to reduce as much as possible the MeOH volume (to ≈10-15 mL). This evaporated crude was basified to pH≈14 with 2M NaOH obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 1.126 g (77%) of a solid was obtained corresponding to the title compound. The isomeric ratio obtained for [5-methyl-1-(naphthalen-2-yl)-1H-pyrazol-3-ol]:[3-methyl-1-(naphthalen-2-yl)-1H-pyrazol-5-ol] was 97:3.

Example 25

Preparation of the Compound of Formula (VII)/ (VIIa) 5-methyl-1-(naphthalen-2-yl)-1H-pyrazol-3-ol via acid chloride of formula (III)

An amount of the compound (IIa) 2-(2,4-dimethyl-1,3-dioxolan-2-yl)acetic acid (5.575 g, 34.77 mmol, 1.35 equiv.) was dissolved in 50 ml of toluene. Under stirring, thionyl chloride (2.5 mL, 34.77 mmol, 1.35 equiv.) was added and the solution was heated at 80° C. for 2 h. After this period of time, the solution was allowed to cool to room temperature and reduced by half the volume of toluene by distillation, thus obtaining a solution of the compound of formula (III) 2-(2,4-dimethyl-1,3-dioxolan-2-yl)acetyl chloride.

This solution of acid chloride in toluene was cannulated over a solution of the compound of formula (IV) naphthalen-2-ylhydrazyne hydrochloride (5.001 g, 25.69 mmol) and $Et_3N$ (10.1 mL, 72.7 mmol) in 20 mL of toluene in ice bath was added dropwise. Once acid chloride was added the cool bath was removed and the mixture was stirred at r.t. for 16 hours. After this period of time, the organic layer was washed with 80 mL of water and dried over $MgSO_4$ and was filtered, and concentrated then to dryness to obtain the compound of formula (V) 2-(2,4-dimethyl-1,3-dioxolan-2-yl)-N'-(naphthalen-2-yl)acetohydrazide.

The dry crude was dissolved in 130 mL of MeOH. A solution of HCl in water (3 mL of concentrated HCl in 7 mL of water) was added to hydrolize the ketal group, thus obtaining the compound of formula (VI) N'-(naphthalen-2-yl)-3-oxobutanehydrazide which subsequently cyclises. The reaction was refluxed for one hour and was allowed to cool to room temperature. The crude was then concentrated in a rotavapor so as to reduce as much as possible the MeOH volume (to ≈10-15 mL). This evaporated crude was basified to pH≈14 with 2M NaOH (≈40 mL) obtaining a precipitate. The basified crude was filtered and the filtrate thus obtained was acidified with dilute AcOH (1:5 with water) to pH≈7. During the neutralisation a new precipitate was observed, which was then filtered and dried in a desiccator. 3.738 g (65%) of a solid was obtained corresponding to the title compound. The isomeric ratio obtained for [5-methyl-1-(naphthalen-2-yl)-1H-pyrazol-3-ol]:[3-methyl-1-(naphthalen-2-yl)-1H-pyrazol-5-ol] was 99.5:0.5.

Example 26 (Comparative)

Adaptation of the process by Ueda et al. 1982 for the preparation of the compound of formula (VII)/(VIIa) 5-methyl-1-(naphthalen-2-yl)-1H-pyrazol-3-ol Naphthalen-2-ylhydrazine hydrochloride (30 g) and NaOMe (20.85 g) were slurried in toluene (300 ml) and heated to 80/85° C. Ethyl 2-(2,4-dimethyl-1,3-dioxolan-2-yl)acetate (30.6 ml) was added and maintained for 90 min Ethyl 2-(2,4-dimethyl-1,3-dioxolan-2-yl)acetate (8.2 ml) and NaOMe (2.5 g) were added and maintained for 2 h. NaOMe (1.7 g) was added and maintained for 1 h. The mixture was cooled to room temperature, water (450 ml) was added and pH adjusted to 6-8 with aqueous HCl. The organic layer was concentrated to dryness under vacuum and methanol (450 ml), HCl 35% (18 ml) and water (54 ml) were added. The mixture was heated to reflux for 90 min and concentrated under vacuum to 165 ml of final volume. Water (120 ml) and CH2Cl2 (120 ml) were added and pH adjusted to 12.2-12.7 (basified with NaOH 25%). Upper organic layer was discarded, and pH of lower aqueous layer was adjusted to 5.0-7.0 with acetic acid 80%. The solid was filtered, washed with water (45 ml) and slurried in ethyl acetate (102 ml) 2 h at 20/25° C. The solid was filtered, washed with ethyl acetate (15 ml) and dried to yield 20.24 g (46%) of a mixture [5-methyl-1-(naphthalen-2-yl)-1H-pyrazol-3-ol]:[3-methyl-1-(naphthalen-2-yl)-1H-pyrazol-5-ol] (80:20).

The invention claimed is:

1. A process for the preparation of a compound of formula (V),

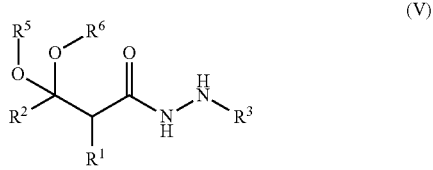

said process comprising the step of:
a1) coupling a compound of formula (II) with a compound of formula (IV) in a suitable solvent, in the presence of a coupling agent, and optionally in the presence of an activating agent of the coupling agent; or

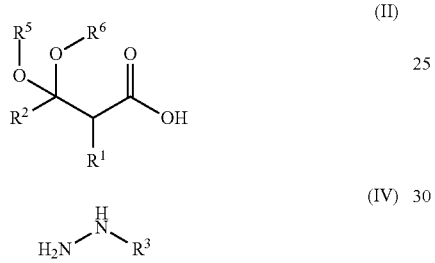

a2) converting a compound of formula (II) into a compound of formula (III) with an activating agent, and coupling said compound of formula (III) with a compound of formula (IV) in a suitable solvent,

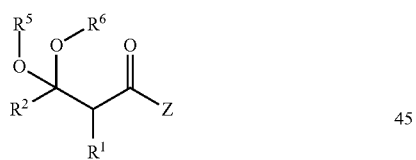

wherein in each of the compounds of formula (II), (III), (IV), and (V), where applicable, $R^1$ is hydrogen or $C_{1-6}$alkyl;

$R^2$ is hydrogen, $C_{1-6}$alkyl, or phenyl;

$R^3$ is naphthyl optionally substituted with one or two substituents selected from halo and $C_{1-6}$alkoxy;

$R^5$ and $R^6$ are, each independently, $C_{1-6}$alkyl, polyhalo$C_{1-6}$alkyl, —C(=O)—$C_{1-6}$alkyl, phenyl, benzyl optionally substituted with nitro; or together with the two oxygen atoms to which they are attached to, form a 4-7 membered heterocyclic ring optionally substituted with one substituent selected from halo, $C_{1-6}$alkyl, $C_{2-6}$alkenyl, polyhalo$C_{1-6}$alkyl, tri$C_{1-6}$alkylsilyl, di$C_{1-6}$alkylphenylsilyl, $C_{1-6}$alkyldiphenylsilyl, tri$C_{1-6}$alkylsilyl$C_{1-6}$alkyl, di$C_{1-6}$alkylphenylsilyl$C_{1-6}$alkyl, $C_{1-6}$alkyldiphenylsilyl$C_{1-6}$alkyl, phenyl optionally substituted with nitro or methoxy, and pyridyl; or the 4-7 membered heterocyclic ring is optionally substituted with two substituents selected from halo and $C_{1-6}$alkyl;

Z represents halo, —O—CO—$R^7$, or —O—CO—O$R^7$; and $R^7$ is $C_{1-4}$alkyl, aryl, or benzyl.

2. The process according to claim 1, wherein the ketal or acetal group of the compound of formula (V) is further cleaved in a suitable solvent;

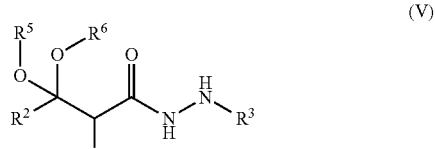

thereby forming a compound of formula (VI),

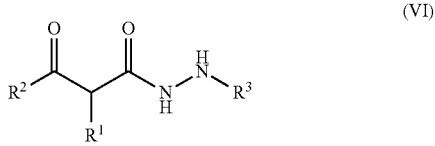

and cyclization of the compound of formula (VI) is allowed, thereby obtaining a compound of formula (VII), a tautomer (VIIa), and salts thereof;

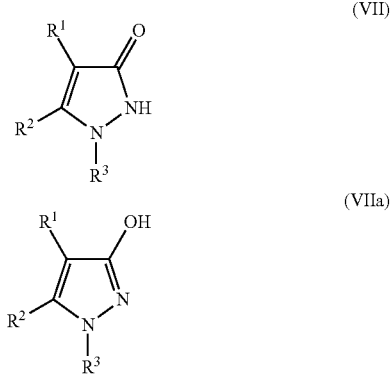

wherein in each of compounds of formula (V), (VI), (VII), and (VIIa), $R^1$, $R^2$, $R^3$, $R^5$, and $R^6$ are as defined in claim 1.

3. A process for the preparation of a compound of formula (VII), a tautomer (VIIa), and salts thereof, as defined in claim 2, said process comprising the steps of:
a1) coupling a compound of formula (II) with a compound of formula (IV) in a suitable solvent, in the presence of a coupling agent, and optionally in the presence of an activating agent of the coupling agent,

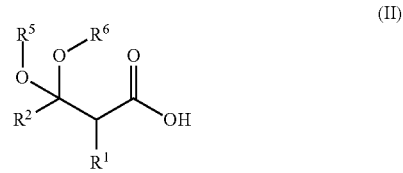

-continued

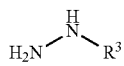
(IV)

or a2) converting a compound of formula (II) into a compound of formula (III) with an activating agent, and coupling said compound of formula (III) with a compound of formula (IV) in a suitable solvent,

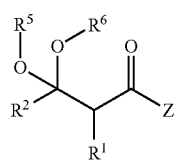
(III)

thereby obtaining a compound of formula (V),

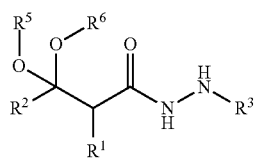
(V)

followed by the cleavage, in the same reaction mixture, of the ketal or acetal group of the compound of formula (V) in a suitable solvent, thereby forming a compound of formula (VI),

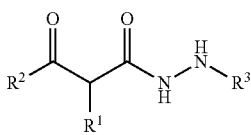
(VI)

and allowing cyclization of the compound of formula (VI), thereby obtaining a compound of formula (VII), a tautomer (VIIa), and salts thereof; wherein in each of compounds of formula (V), (VI), (VII), and (VIIa), $R^1$, $R^2$, $R^3$, $R^5$, $R^6$, $R^7$, and Z are as defined in claim 1.

4. The process according to claim 1, wherein the compound of formula (IV) is obtained by reacting a salt of the compound of formula (IV) with a base.

5. The process according to claim 4, where the reaction of a salt of compound of the formula (IV) with a base is performed in the same reaction mixture of claim 1.

6. The process according to claim 1, wherein the coupling agent in step a1) is a carbodiimide, preferably dicyclohexylcarbodiimide (DCC), diisopropylcarbodiimide (DIC), or N-ethyl-N'-[(3dimethylamino)propyl]carbodiimide (EDC).

7. The process according to claim 1, wherein the activating agent of the coupling agent in step a1) is selected from 1-hydroxybenzotriazole (HOBt) and 4-dimethylaminopyridine (4-DMAP).

8. The process according to claim 1, wherein the activating agent in step a2) is selected from a halogenating agent, $C_{1-4}$alkyl acid halide, aryl acid halide, benzyl acid halide, $C_{1-4}$alkyl haloformate, aryl haloformate, and benzyl haloformate.

9. The process according to claim 1, wherein the compound of formula (II) is prepared by cleaving $R^4$ from compound of formula (I),

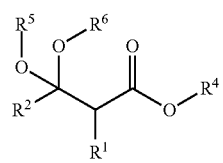
(I)

wherein in compound of formula (I), $R^1$, $R^2$, $R^5$, and $R^6$ are as defined in claim 1; and $R^4$ is $C_{1-6}$alkyl, aryl, or benzyl.

10. The process according to claim 2, wherein the cleavage of the ketal or acetal group of compound of formula (V) is performed by acidic treatment in an aqueous medium, an organic solvent, or a mixture thereof.

11. A compound of formula (VI), a salt, or stereoisomer thereof,

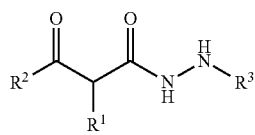
(VI)

wherein, $R^1$, $R^2$, and $R^3$ are as defined in claim 1.

12. A compound of formula (V), a salt, or stereoisomer thereof,

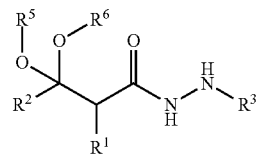
(V)

wherein, $R^1$, $R^2$, and $R^3$ are as defined in claim 1; and $R^5$ and $R^6$ are, each independently, $C_{1-6}$alkyl, polyhalo$C_{1-6}$alkyl, acetyl, phenyl, benzyl, 2-nitrobenzyl; or together with the two oxygen atoms to which they are attached to, form a 4-7 membered heterocyclic ring optionally substituted with one substituent selected from halo, $C_{1-6}$alkyl, $C_{2-6}$alkenyl, halo$C_{1-6}$alkyl, trimethylsilyl, trimethylsilylmethyl, phenyl, 2-nitrophenyl, 4-methoxyphenyl, 2-pyridyl; or the 4-7 membered heterocyclic ring is optionally substituted with two substituents selected from halo and $C_{1-6}$alkyl.

13. A compound of formula (III), a salt, or stereoisomer thereof,

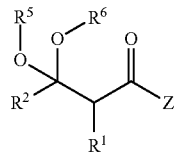

(III)

wherein, $R^1$ is hydrogen or $C_{1-6}$alkyl;

$R^2$ is hydrogen, $C_{1-6}$alkyl, or phenyl;

$R^5$ and $R^6$ are, each independently, ethyl, butyl, or together with the two oxygen atoms to which they are attached to, form a 4-7 membered heterocyclic ring substituted with one or more substituents selected from halo, $C_{1-6}$alkyl, $C_{2-6}$alkenyl, polyhalo$C_{1-6}$alkyl, tri$C_{1-6}$alkylsilyl, di$C_{1-6}$alkylphenylsilyl, $C_{1-6}$alkyldiphenylsilyl, tri$C_{1-6}$alkylsilyl$C_{1-6}$alkyl, di$C_{1-6}$alkylphenylsilyl$C_{1-6}$alkyl, $C_{1-6}$alkyldiphenylsilyl$C_{1-6}$alkyl, phenyl optionally substituted with nitro or methoxy, and pyridyl; or the 4-7 membered heterocyclic ring is substituted with two substituents selected from halo and $C_{1-6}$alkyl;

Z represents halo, —O—CO—$R^7$, or —O—CO—O$R^7$; and $R^7$ is $C_{1-4}$alkyl, aryl, or benzyl.

14. A compound of formula (II), a salt, or a stereoisomer thereof,

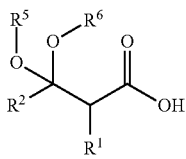

(II)

wherein $R^1$ is hydrogen;

$R^2$ is methyl;

$R^5$ and $R^6$ are, each independently, $C_{3-7}$alkyl; or together with the two oxygen atoms to which they are attached to, form a 4-7 membered heterocyclic ring substituted with one substituent selected from halo, $C_{1-6}$alkyl, $C_{2-6}$alkenyl, polyhalo$C_{1-6}$alkyl, tri$C_{1-6}$alkylsilyl, di$C_{1-6}$alkylphenylsilyl, $C_{1-6}$alkyldiphenylsilyl, tri$C_{1-6}$alkylsilyl$C_{1-6}$alkyl, di$C_{1-6}$alkylphenylsilyl$C_{1-6}$alkyl, $C_{1-6}$alkyldiphenylsilyl$C_{1-6}$alkyl, phenyl optionally substituted with nitro or methoxy, and pyridyl; or the 4-7 membered heterocyclic ring is substituted with one halo and one $C_{1-6}$alkyl.

15. A method for the preparation of a compound of formula (X),

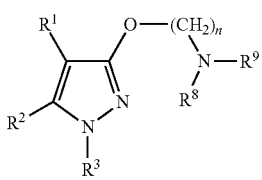

(X)

wherein, $R^1$, $R^2$, and $R^3$ are as defined in claim 1;

n is 2, 3, or 4; and $R^8$ and $R^9$ are, each independently, $C_{1-6}$alkyl, $C_{1-6}$alkoxy$C_{1-6}$alkyl, benzyl, or together with the nitrogen atom to which they are attached to, form a morpholinyl optionally substituted with $C_{1-6}$alkyl; thiomorpholinyl; piperazinyl optionally substituted with $C_{1-6}$alkyl, $C_{1-6}$alkylcarbonyl, or $C_{1-6}$alkoxycarbonyl; piperidinyl optionally substituted with $C_{1-6}$alkylcarbonyl, phenyl, or 3H-imidazo[4,5-b]pyridinyl; pyrrolidinyl optionally substituted with amino or $C_{1-6}$alkylcarbonylamino; pirazolinyl; 1,2,3,4-tetrahydroisoquinolinyl; or 3H-imidazo[4,5-b]pyridinyl;

which comprises employing a compound of formula (VI), (V), (III), (II), (I), a salt, or stereoisomer thereof.

* * * * *